(12) United States Patent
Yang et al.

(10) Patent No.: US 9,738,893 B2
(45) Date of Patent: Aug. 22, 2017

(54) METHOD OF ENHANCING MIR-185 EXPRESSION TO REDUCE LOW DENSITY LIPOPROTEIN/CHOLESTEROL ACCUMULATION IN A CELL

(71) Applicants: Muhua Yang, Hamilton, NJ (US); Joseph T. Nickels, Robbinsville, NJ (US); Weidong Liu, Chesterbrook, PA (US); Christina Ann Pellicane, Edison, NJ (US)

(72) Inventors: Muhua Yang, Hamilton, NJ (US); Joseph T. Nickels, Robbinsville, NJ (US); Weidong Liu, Chesterbrook, PA (US); Christina Ann Pellicane, Edison, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 15/004,104

(22) Filed: Jan. 22, 2016

(65) Prior Publication Data

US 2016/0194635 A1 Jul. 7, 2016

Related U.S. Application Data

(63) Continuation of application No. 13/919,141, filed on Jun. 17, 2013, now Pat. No. 9,243,250.

(60) Provisional application No. 61/660,057, filed on Jun. 15, 2012.

(51) Int. Cl.
*C12N 15/11* (2006.01)
*C12N 15/113* (2010.01)
*C12Q 1/68* (2006.01)

(52) U.S. Cl.
CPC ........ *C12N 15/113* (2013.01); *C12N 15/1137* (2013.01); *C12N 15/1138* (2013.01); *C12Q 1/6883* (2013.01); *C12N 2310/141* (2013.01); *C12Q 2600/158* (2013.01); *C12Q 2600/178* (2013.01); *C12Y 101/01034* (2013.01); *C12Y 205/01021* (2013.01)

(58) Field of Classification Search
CPC ..................... C12N 15/113; C12N 2310/141
See application file for complete search history.

(56) References Cited

U.S. PATENT DOCUMENTS

2013/0143764 A1* 6/2013 Ogier-Denis ........ C12Q 1/6883
506/9
2015/0005365 A1* 1/2015 Zakharenko ........ C12Q 1/6883
514/44 A

OTHER PUBLICATIONS

Yang et al. Journal of Lipid Research 55, 2014 226-238.*
Liao et al. (The Journal of Biological Chemsitry, 286, 33901-33909, Sep. 30, 2011).*
Liu et al. Cancer Letters 301 2011 151-160.*

* cited by examiner

*Primary Examiner* — Brian Whiteman
(74) *Attorney, Agent, or Firm* — Siu K. Lo; Jessica A. Downing

(57) ABSTRACT

The present invention provides a method of quantifying miR-185 as a potential biomarker in lipid disorder or cardiovascular diseases in human. The present invention also provides a method of modulating miR-185 in regulating LDL and cholesterol metabolism in cells. The present invention has therapeutic potential in the treatment of cholesterol/LDL related cardiovascular diseases in humans.

3 Claims, 21 Drawing Sheets

Fig. 1A

Human SREBF2 NM_004599 3'UTR (SEQ ID NO: 3) Length: 709 bp

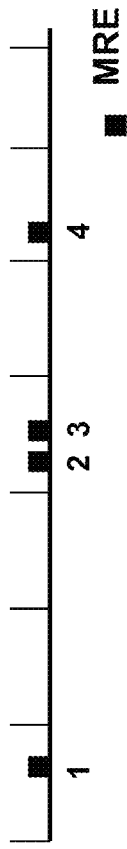

■ MRE

Fig. 1B

C→G mutations within four miR185 MREs:

1) WT:  45 CTCT<u>C</u>TCT<u>C</u>CCC 59      (bp 45-59 of SEQ ID NO: 3)
   Mut: 45 CTCT<u>G</u>TCT<u>G</u>CCC 59      (bp 45-59 of SEQ ID NO: 4)

2) WT:  388 TCT<u>C</u>TCT<u>C</u>CTG 400    (bp 388-400 of SEQ ID NO: 3)
   Mut: 388 TCT<u>G</u>T<u>G</u>T<u>G</u>CTG 400    (bp 388-400 of SEQ ID NO: 4)

3) WT:  407 ACT<u>C</u>T<u>C</u>T<u>C</u>CTT 419   (bp 407-419 of SEQ ID NO: 3)
   Mut: 407 ACT<u>G</u>T<u>G</u>T<u>G</u>CTT 419   (bp 407-419 of SEQ ID NO: 4)

4) WT:  638 ATT<u>C</u>T<u>C</u>T<u>C</u>CCT 650   (bp 638-650 of SEQ ID NO: 3)
   Mut: 638 ATT<u>G</u>T<u>G</u>T<u>G</u>CCT 650   (bp 638-650 of SEQ ID NO: 4)

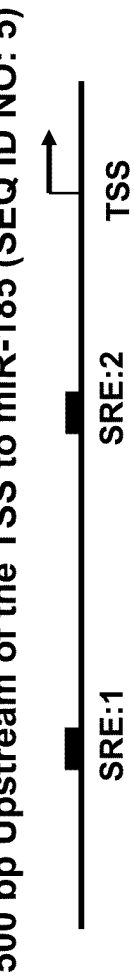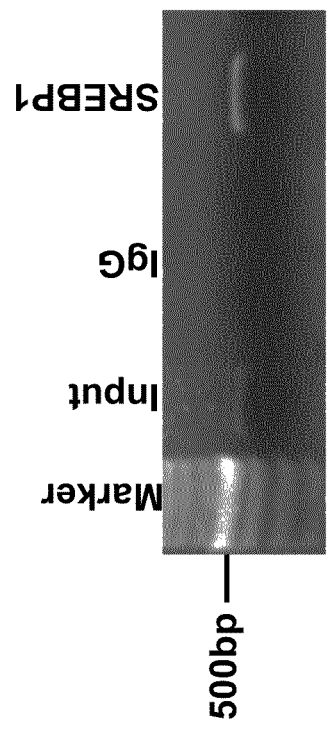
Fig. 11A 500 bp Upstream of the TSS to miR-185 (SEQ ID NO: 5)
Fig. 11B SRE in the Promoter Region of miR-185
Site 1: -356 gcctggtactcacctgaggttatta -330 (-356 bp to -330 bp of SEQ ID NO: 5)
Site 2: -133 ctggagctctcaggccacctgccc -109 (-133 bp to -109 bp of SEQ ID NO: 5)
Fig. 11C

SEQUENCE LISTING

```
<160> NUMBER OF SEQ ID NOS: 18

<210> SEQ ID NO 1
<211> LENGTH: 82
<212> TYPE: RNA
<213> ORGANISM: Homo sapiens
<220> FEATURE:
<221> NAME/KEY: misc_RNA
<222> LOCATION: (1)..(82)
<223> OTHER INFORMATION: microRNA

<400> SEQUENCE: 1 aggggggcgag ggauuggaga gaaaggcagu uccugauggu ccccucccca ggggcuggcu      60
uuccucuggu ccuucccucc ca                                               82

<210> SEQ ID NO 2
<211> LENGTH: 22
<212> TYPE: RNA
<213> ORGANISM: Homo sapiens
<220> FEATURE:
<221> NAME/KEY: misc_RNA
<222> LOCATION: (1)..(22)
<223> OTHER INFORMATION: microRNA

<400> SEQUENCE: 2
uggagagaaa ggcaguuccu ga                                               22

<210> SEQ ID NO 3
<211> LENGTH: 709
<212> TYPE: DNA
<213> ORGANISM: Homo sapiens

<400> SEQUENCE: 3
ccaccaggct cagcccaccc ctccacctct ctctcgattt ctctctctcc ccctcagcat      60
cttcccgctg agagtggtgg ggaagagcct tgtcttctta gctgtcacct gccgaggctt     120
ctgggccact caggccagtg cacccctggg cagagcccct taaagctgct gtcactagat     180
gcccatggtc cagggcctgg tgggcgtgag aggataggtg gcagggcaga aactgggcag     240
```

```
ccctgacttg atagcagcag ggggagctcc caagctgcca agccctgcc tccagccttc    300
ctgagtttct ctctcctgaa ccctactctc tccttttgc ttcctcagtt tttatcaggc    360
tttctctggg ggacagcagt ctctgagcac cagggagcag ttgccctcag gcctgtgccc    420
agcatgccct ccccttttta tacgaatgtt ttctaccagt gtgcttgggt ttgccatgat    480
gcgaggctga gttgctgtag cgtcttgatt ctctccctgg gtctgcgttc cctcccctgg    540
gcctgactga gcctgctcat tgttttttccc tttattacac aggacagcca ggggaggagg    600
ggggcccagc cctgggaggc tggtgggagg caggggggcag gcctgcggat gcatgaaata    660
atgttggcat tattttttaa tttttttaaaa aataaatggt atcttattt                709
```

<210> SEQ ID NO 4
<211> LENGTH: 709
<212> TYPE: DNA
<213> ORGANISM: Homo sapiens

<400> SEQUENCE: 4

```
ccaccaggct cagcccaccc ctccacctct ctctcgattt ctctgtctgc ccctcagcat     60
cttcccgctg agagtggtgg ggaagagcct tgtcttctta gctgtcacct gccgaggctt    120
ctgggccact caggccagtg cacccctggg cagagcccct aaagctgct gtcactagat     180
gcccatggtc cagggcctgg tgggcgtgag aggataggtg gcagggcaga aactgggcag    240
ccctgacttg atagcagcag ggggagctcc caagctgcca agccctgcc tccagccttc    300
ctgagtttct gtgtgctgaa ccctactgtg tgcttttgc ttcctcagtt tttatcaggc    360
tttctctggg ggacagcagt ctctgagcac cagggagcag ttgccctcag gcctgtgccc    420
agcatgccct ccccttttta tacgaatgtt ttctaccagt gtgcttgggt ttgccatgat    480
gcgaggctga gttgctgtag cgtcttgatt gtgtgcctgg gtctgcgttc cctcccctgg    540
gcctgactga gcctgctcat tgttttttccc tttattacac aggacagcca ggggaggagg    600
ggggcccagc cctgggaggc tggtgggagg caggggggcag gcctgcggat gcatgaaata    660
atgttggcat tattttttaa tttttttaaaa aataaatggt atcttattt                709
```

<210> SEQ ID NO 5
<211> LENGTH: 500
<212> TYPE: DNA
<213> ORGANISM: Homo sapiens

<400> SEQUENCE: 5

```
tcccagagta aaggcagata aggcagtagt taagaagtag gaagaagtaa aggcagctac     60
cccagagaag ctaaggtcgg gagaggtgga ggctcccact gcaccccct ggcccatacc    120
atagggagg tttcccccac agcagcctgg gtactcacct gaggttatta gacagcagca    180
ttaagagcct actctaaaaa ataccccacgg ggcacctttc ttttccttat ttctaaatat    240
gcctggatgt agggaaaggg agctgaagtc ctttagttcc atttttaagta tgttacatta    300
cacatagcta agaaacggtg aaatattgta agcagccaat atttaattat ttaaaaatta    360
aaataggctg gagctctcag gccacctgcc cagggcgact ccccagcaaa ccgagcagtc    420
tccctcagag tggagatgac atgtctccgc accggcaccg agggggcgca gggcggcgtg    480
gggagggga cccaggccgg                                                  500
```

<210> SEQ ID NO 6
<211> LENGTH: 24
<212> TYPE: DNA

<213> ORGANISM: Homo sapiens

<400> SEQUENCE: 6
atcccagagt aaaggcagat aagg                                          24

<210> SEQ ID NO 7
<211> LENGTH: 19
<212> TYPE: DNA
<213> ORGANISM: Homo sapiens

<400> SEQUENCE: 7
gcggagacat gtcatctcc                                                19

<210> SEQ ID NO 8
<211> LENGTH: 40
<212> TYPE: DNA
<213> ORGANISM: Homo sapiens

<400> SEQUENCE: 8
cagcagcctg ggtactcacc tgaggttatt agacagcagc                         40

<210> SEQ ID NO 9
<211> LENGTH: 40
<212> TYPE: DNA
<213> ORGANISM: Homo sapiens

<400> SEQUENCE: 9
gctgctgtct aataacctca ggtgagtacc caggctgctg                         40

<210> SEQ ID NO 10
<211> LENGTH: 40
<212> TYPE: DNA
<213> ORGANISM: Homo sapiens

<400> SEQUENCE: 10
cagcagcctg ggtaccggca ggaggttatt agacagcagc                         40

<210> SEQ ID NO 11
<211> LENGTH: 40
<212> TYPE: DNA
<213> ORGANISM: Homo sapiens

<400> SEQUENCE: 11
gctgctgtct aataacctcc tgccggtacc caggctgctg                         40

<210> SEQ ID NO 12
<211> LENGTH: 40
<212> TYPE: DNA
<213> ORGANISM: Homo sapiens

<400> SEQUENCE: 12
gaggctggag ctctcaggcc acctgcccag ggcgactccc                         40

<210> SEQ ID NO 13
<211> LENGTH: 40
<212> TYPE: DNA
<213> ORGANISM: Homo sapiens

<400> SEQUENCE: 13
gggagtcgcc ctgggcaggt ggcctgagag ctccagcctc                         40

<210> SEQ ID NO 14
<211> LENGTH: 40

```
<212> TYPE: DNA
<213> ORGANISM: Homo sapiens

<400> SEQUENCE: 14
gaggctggag ctcctcgcct cgatgcccag ggcgactccc                           40

<210> SEQ ID NO 15
<211> LENGTH: 40
<212> TYPE: DNA
<213> ORGANISM: Homo sapiens

<400> SEQUENCE: 15
gggagtcgcc ctgggcatcg aggcgaggag ctccagcctc                           40

<210> SEQ ID NO 16
<211> LENGTH: 641
<212> TYPE: DNA
<213> ORGANISM: Homo sapiens

<400> SEQUENCE: 16
cgcccagatc aagatatggt gaccaaaagg acaaggacta tatccatggc tccctcccag     60
agcctggcaa gtcagcaggc atgagagggt gttggaatgc tgtggtgggc ctgtgtgggg    120
accttgtagg acctagggaa cctgcagggc ttggcttagg gagcacacag gggcccaggc    180
aaaggcaagg tcacaggtcg ggggaggtga agctggcagg gggaggggga gacctgctgg    240
ctagagctgg gttgggggcc ggtgggcagt gggcctggct cgagcagggg gcgagggatt    300
ggagagaaag gcagttcctg atggtcccct ccccaggggc tggctttcct ctggtccttc    360
cctcccaatg accgcgtctt cgtcgaggcc acagcccttg gctctgcgcc cacacctcca    420
gtgccaggct gtccggagat ctgtttatgg ccttcccttg gaccatggag ccctccctgc    480
cactggtgcc tggagggctg gtctgctgcc cctgcaccct ggccagctag gatggtgggg    540
tcctgcagct gaactggggg tgcctttctg cctgtctgtc ctacgtgtat cagtggccag    600
aactgccctc atccatggcc ttgccagcag ctgggcgtgc a                        641

<210> SEQ ID NO 17
<211> LENGTH: 26
<212> TYPE: DNA
<213> ORGANISM: Homo sapiens

<400> SEQUENCE: 17
gaattccgcc cagatcaaga tatggt                                          26

<210> SEQ ID NO 18
<211> LENGTH: 22
<212> TYPE: DNA
<213> ORGANISM: Homo sapiens

<400> SEQUENCE: 18
ggatcctgca cgcccagctg ct                                              22
```

METHOD OF ENHANCING MIR-185 EXPRESSION TO REDUCE LOW DENSITY LIPOPROTEIN/CHOLESTEROL ACCUMULATION IN A CELL

CROSS-REFERENCE TO RELATED APPLICATIONS

The present application is a continuation of issued U.S. Pat. No. 9,243,250 filed on Jun. 17, 2013, which claims benefit under 35 U.S.C. §119(e) to U.S. Provisional Application No. 61/660,057 filed on Jun. 15, 2012, the contents of which are herein incorporated by reference in their entireties.

FIELD OF THE INVENTION

The present invention generally relates to the field of modulating miR-185 in a cell so as to regulate SREBP-2 expression and hence reducing cholesterol/low-density lipoprotein (LDL) metabolism. Specifically, the present invention provides a method of enhancing miR-185 in a cell, whose enhanced miR-185 level is targeted in inhibiting enzymes that are central to cholesterol synthesis as well as reducing low-density lipoprotein receptor (LDLR) and LDL uptake in the cell. The present invention also provides a method of determining the expression levels of miR-185 and cholesterol in humans suspected of suffering from atherosclerosis and provides a correlation between elevated expression levels of miR-185 and cholesterol and atherosclerosis and use of same in predicting increased risk atherosclerosis in humans.

BACKGROUND OF THE INVENTION

Dysregulation of cholesterol homeostasis in vascular cells is a key feature in cardiovascular diseases including atherosclerosis (Sani et al., 2004). Elevated cholesterol biosynthesis in cells is attributed to high blood cholesterol, leading to an increased production of very-low density lipoprotein (VLDL), low-density lipoprotein (LDL) and high-density lipoprotein (HDL) (Glass, et al., 2001). The accumulation of these lipoproteins, in particular LDL, is believed to induce the transformation of macrophages/vascular smooth muscle cells to foam cells through the uptake of LDL by the LDL receptor, which eventually triggers atherosclerotic plaque formation. It would be ideal to reduce LDL accumulation to ameliorate foam cell progression.

The current remedy in the treatment of high blood cholesterol is statins. Statins inhibit the HMG-CoA reductase enzyme that catalyzes the rate-limiting step in cholesterol biosynthesis, and thus lowering the cholesterol synthesis (Shefer, et al., 1972). The intracellular biosynthetic cholesterol concentration is tightly regulated by a feedback mechanism that involves the regulation of the sterol response element transcription factor protein (SREBP) (Brown, et al., 1997). The SREBP families of proteins are basic-helix-loop-helix leucine zipper transcription factors. SREBP-1a, SREBP-1c, and SREBP-2 proteins are encoded by two distinct genes, SREBF-1 and SREBF-2 (Gasic, et al., 1994). SREBP-2 is the critical regulator of cholesterol biosynthesis through its transcriptional regulation of multiple cholesterol genes, including HMG-CoA reductase (HMGCR), farnesyl-diphosphate farnesly transferase (squalene synthase; FDFT1), and LDLR (Brown, et al., 1997; Shimomura, et al., 1997).

The underlying mechanism that regulates SREBP-2 activity is poorly understood. There is little information as to whether SREBP-2 expression may be post-transcriptionally regulated by microRNAs (miRNAs), although aberrant expression of certain miRs is suggested to be associated with cardiovascular diseases.

Accordingly, there is a continuing need to understand if there is an association between specific miRNAs and pathogenesis of lipid dysregulation. The present invention provides a novel approach of enhancing miR-185 in a cell so as to regulate SBEBP-2, thus regulating LDLR and LDL uptake as well as cholesterol synthesis in the cell. The present invention also provides the use miR-185 in predicting cardiovascular diseases in humans.

SUMMARY OF THE INVENTION

In one aspect, the present invention provides a method of treating a human cell in need of reducing LDL and cholesterol accumulation, comprising the steps of: a) providing a human cell in need of reducing LDL and cholesterol accumulation; and b) transfecting in said cell a miR-185 precursor to cause an increase in miR-185 expression, said miR-185 precursor consisting of a nucleotide sequence set forth in SEQ ID NO: 1, wherein said increased miR-185 expression in said cell leads to: (i) inhibition of HMGCR, (ii) inhibition of squalene synthase, and (iii) reduced expression of LDLR, thereby reduce LDL and cholesterol accumulation in said cell.

Preferably, the human cell is a liver cell, vascular smooth muscle cell and macrophage. More preferably, the human cell is a liver cell.

Preferably, the transfecting step is performed using electroporation, DEAE-dextran, calcium phosphate, or cationic liposome.

In another aspect, the present invention provides a method of reducing LDL and cholesterol accumulation in a human cell, comprising the steps of: a) providing a human cell in need of reducing LDL and cholesterol accumulation; and b) transfecting said cell with a miR-185 precursor so as to increase miR-185 expression in said cell, wherein said increased miR-185 expression causes a reduction of LDL and cholesterol accumulation in said human cell.

Preferably, the miR-185 precursor consists the sequence set forth in SEQ ID NO: 1.

In another aspect, the present invention provides a method for inhibiting the expression level of at least a gene selected from the group consisting of HMGCR, squalene synthase, and LDLR in a cell, comprising the step of transfecting in said cell with a composition comprising a miR-185 precursor, said miR-185 precursor consisting of a nucleotide sequence set forth in SEQ ID NO: 1.

In yet another aspect, the present invention provides a method for predicting an increased risk of atherosclerosis in a patient comprising: (a) determining the level of cholesterol in a blood or serum sample; and (b) determining the level of miR-185 in said blood or serum sample, wherein an increased level of cholesterol level and miR-185 when compared to a control blood or serum ample, is indicative of an increased risk of atherosclerosis in said patient.

Various objects and advantages of this invention will become apparent to those skilled in the art from the following detailed description of the preferred embodiment, when read in light of the accompanying drawings and claims.

BRIEF DESCRIPTION OF THE DRAWINGS

FIGS. 1A and 1B depict the wild-type miR-185 microRNA response elements (MREs) present within the SREBP-2 mRNA 3'UTR (SEQ ID NO: 3) (709 bp) and the four (4) MREs within the SREBP-2 mRNA 3'UTR containing the four (4) site mutations (SEQ ID NO: 4). FIG. 1A depicts a schematic depiction of the SREBP-2 3'UTR and the relative location of the four (4) predicted miR-185 MRE sites. FIG. 1B depicts a SREBP-2 3'UTR mutant generated by site-directed mutagenesis of the four (4) miR-185 MREs (i.e., mutating each C to G within the four (4) MREs). Specifically, the SREBP-2 3'UTR mutant contains: (i) the 45 bp and 49 bp locations (C→G); (ii) the 311 bp, 313 bp and 315 bp locations (C→G); (iii) the 328 bp, 330 bp, and 332 bp locations (C→G); and (iv) the 511 bp, 513 bp, and 515 bp locations (C→G) of the wild-type SREBP-2 mRNA 3'UTR. The SREBP-2 3'UTR mutant has a nucleotide sequence set forth in the SEQ ID NO: 4.

FIG. 3A shows the fold change in SREBP-2 mRNA was measured by qRT-PCR in pre-miR-185 (SEQ ID NO: 1), pre-miR-185+antagomiR-185, or control miR transfected HepG2 cells. FIG. 3B shows the SREBP-2 mRNA was measured by qRT-PCR in pre-miR-185, pre-miR-185+antagomiR-185 or control miR transfected THLE-2 cells. Values were normalized to the level of GAPDH. Bar graphs represent mean±s.e.m from three independent experiments. (*Significant as compared to controls (P<0.02)).

FIG. 5A depicts a qRT-PCR used to quantitate farnesyl-diphosphate farnesyl transferase (FDFT1) mRNA level in HepG2 cells transfected with pre-miR-185 or control miR. (*Significant as compared to controls (P<0.01)). FIG. 5B depicts the control pre-miR or pre-miR-185 transfected cells treated with Methyl-β-cyclodextrin (MCD). FDFT1 mRNA levels were compared to control transfected HepG2 without MCD treatment by qRT-PCR. GAPDH was used as internal control. (*Significant as compared to controls (P<0.05)). Bar graphs represent mean±s.e.m from three independent experiments.

FIG. 6A and FIG. 6B depict a qRT-PCR used to measure low density lipoprotein receptor (LDLR) and HMG-CoA reductase (HMGCR) mRNA level in HepG2 cells with or without the over-expression of miR-185 and with the presence and absence of MCD (as described in FIG. 5). GAPDH was used as internal control. Bar graphs represent mean±s.e.m from three independent experiments. (*Significant as compared to controls (P<0.01)).

FIG. 7A depicts LDLR protein level examined in HepG2 cells transfected with 100 nM of control miR or pre-miR-185 by Lipofectamine® 2000. Western blot was performed 48 hours post transfection. β-actin was used as loading control. FIG. 7B depicts cell surface LDLR stained by immunocytochemistry in HepG2 cells transfected with control miR or pre-miR-185 where 4',6-diamidino-2-phenylindole (DAPI) was used as a counter staining and Leica DMI6000 fluorescent microscopy was used to visualize the staining.

FIGS. 11A, 11B, and 11C depict SREBP-1c as a transcriptional regulator of miR-185. FIG. 11A depicts the putative promoter region (500 bp) (SEQ ID NO: 5) upstream of the transcriptional starting site (TSS) to miR-185 that contains two (2) sterol response element (SRE) binding sites. FIG. 11B depicts the two putative SREs sequences. The first SRE within the promoter region of miR-185 transcript is located within the -356 bp to -330 bp. The second SRE within the promoter region of the miR-185 transcript is located within the -133 bp to -109 bp. FIG. 11C depicts a ChIP assay used to determine the interaction between SREBP-1c and the miR-185 promoter region. 10% of the cell lysis was used as input and rabbit IgG was used as negative control. Primers to detect 50 bp to 500 bp upstream from the transcriptional starting site (TSS) of miR-185 were used for the PCR.

Figure 2:
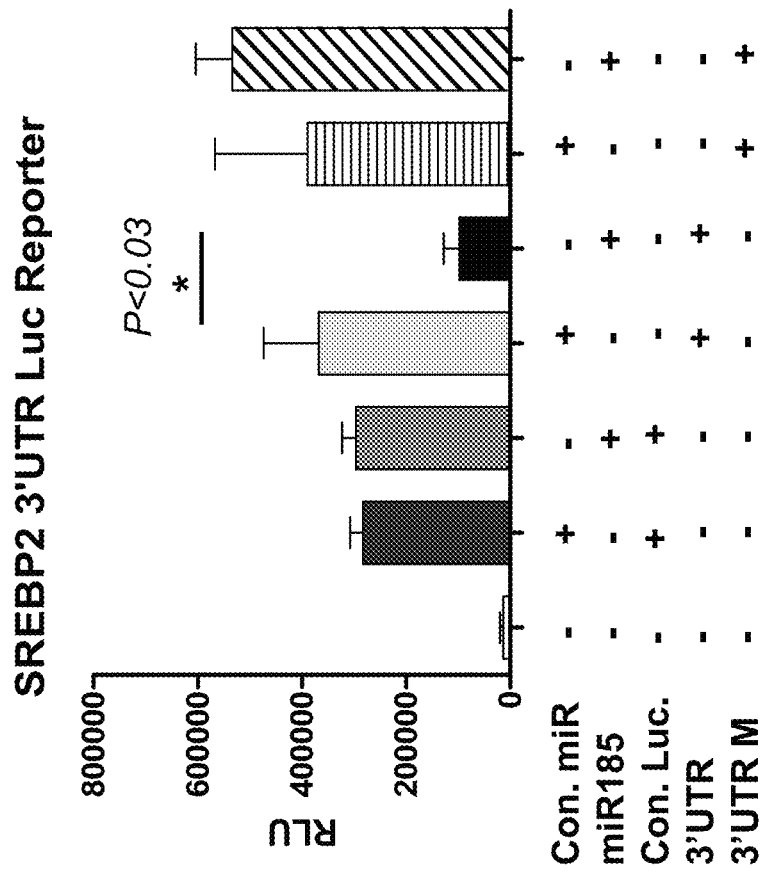
FIG. 2 depicts miR-185 binding to the MREs of the SREBP-2 mRNA 3'UTR. The binding was monitored by luciferase activity quantitated in 293T cells (human embryonic kidney cells) transfected with control LightSwitch luciferase reporter plasmid (Con Luc), SREBP-2 3'UTR containing reporter plasmid (3' UTR) that has SEQ ID NO: 3, SREBP-2 3'UTR mutant (3' UTRM) that has SEQ ID NO: 4. These cells were also co-transfected with either pre-miR-185 (miR185) (SEQ ID NO: 1) or control pre-miR (Con miR). Luciferase activity was measured in 293T cells as described in the Experimental Methods and Protocols section. Bar graphs represent mean±s.e.m from three independent experiments. (*Significant as compared to control (P<0.03)).

WT SRE probe; lane 3: mutant SRE probe; lane 4: WT putative SRE probe; and lane 5: mutant putative SRE probe. The DNA-protein complex formation is shown in lane 2. Free probe was used as control (lane 1).

Figure 13:
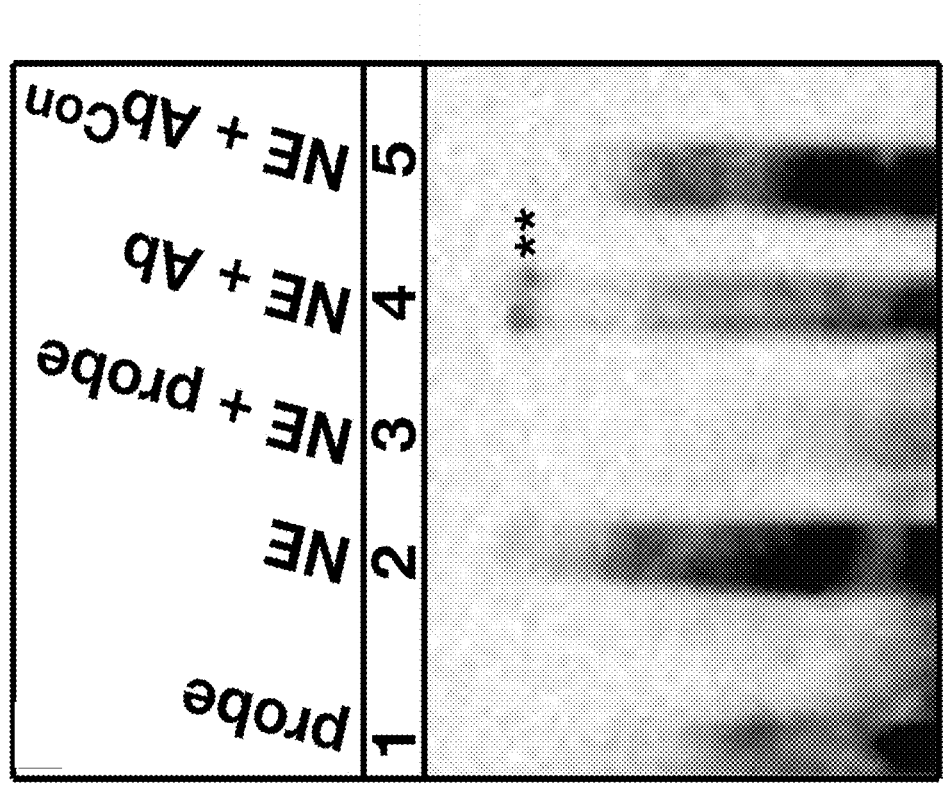

FIG. 13 depicts SREBP-1c binding to SRE within the miR-185 promoter. An electrophoretic mobility shift assay (EMSA) was used and SREBP-1c was determined to bind to SRE within the miR-185 promoter. HepG2 nuclear extract was incubated in the presence of: lane 1: free probe; lane 2: WT SRE probe; lane 3: WT SRE probe competitor; lane 4: SREBP-1c antibodies; and lane 5: GAPDH antibody. The supershift induced by SREBP-1c antibody binding to SREBP-1c in the nuclear extract is shown in lane 4. Free probe was used as control (lane: 1). GAPDH antibody was used as negative control of SREBP-1c antibody interaction (lane: 5). **indicates the supershift caused by SREBP-1c antibody binding to nuclear SREBP-1c-SRE probe complex.

Figure 14A:
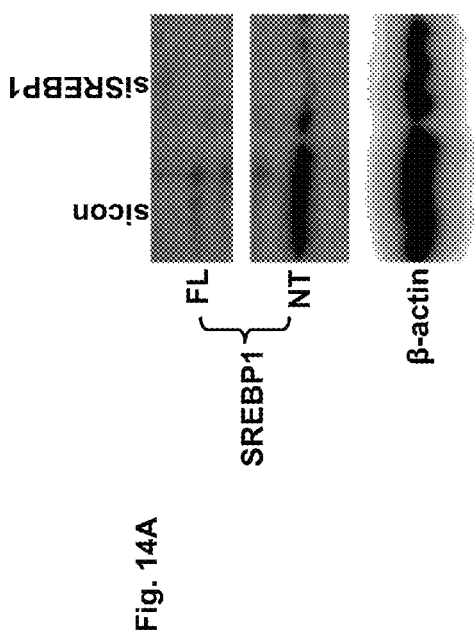
Figure 14C:
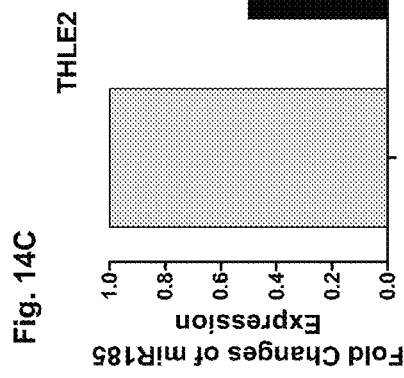
Figure 14B:
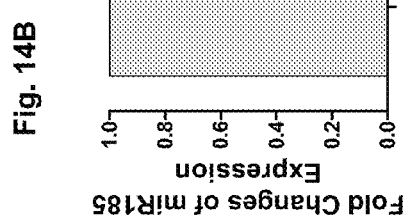

FIGS. 14A, 14B, and 14C depict SREBP-1c regulating miR-185 expression level in human liver cells. FIG. 14A depicts a Western blot where SREBP-1c protein expression was observed in both HepG2 cells transfected with 100 nM of each SREBP-1c siRNA (Invitrogen, catalog no. 4390824) and in control siRNA (Invitrogen, catalog no. 4390843). β-actin was used as loading control. FIG. 14B depicts a comparison between the observed fold changes of mature miR-185 levels in SREBP-1c siRNA transfected with HepG2 cells and cells transfected with control siRNA, which were quantitated by qRT-PCR. FIG. 14C depicts a comparison between the observed fold changes of THLE-2 cells and cells transfected with control siRNA, which were quantitated by qRT-PCR. RNU6-2 was used as internal control. Bar graphs represent mean±s.e.m from three independent experiments. (*Significant as compared to controls ($P<0.01$)).

Figure 15B:
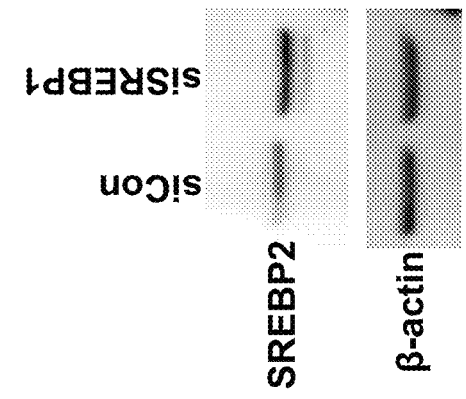
Figure 15A:
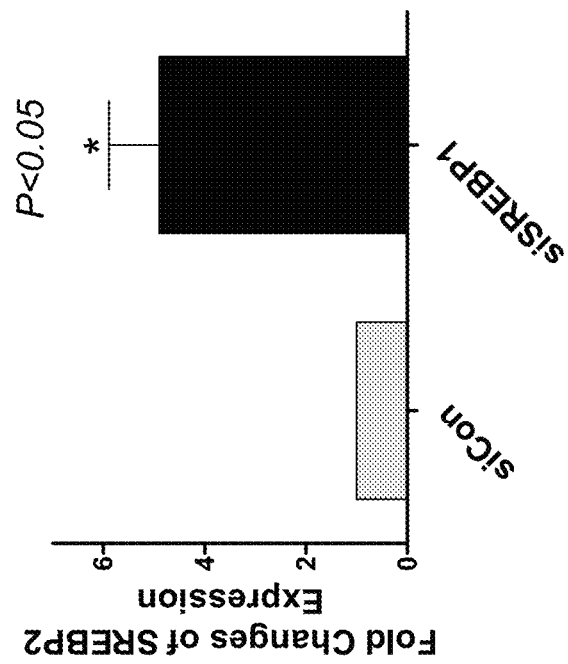

FIGS. 15A and 15B depict SREBP-1c mediating SREBP-2 expression in human liver cells when miR-185 transcription is regulated. FIG. 15A depicts the fold changes of SREBP-2 mRNA in HepG2 cells transfected with 100 nM of each SREBP-1c siRNA and control siRNA (Invitrogen, catalog no. 4390843). FIG. 15B depicts a Western blot of SREBP-2 protein level in HepG2 cells transfected with SREBP-1 siRNA and control siRNA. GAPDH was used as internal control in qRT-PCR. β-actin was used as loading control in Western blotting. Bar graphs represent mean±s.e.m from three independent experiments. (*Significant as compared to controls ($P<0.01$)).

Figure 16:
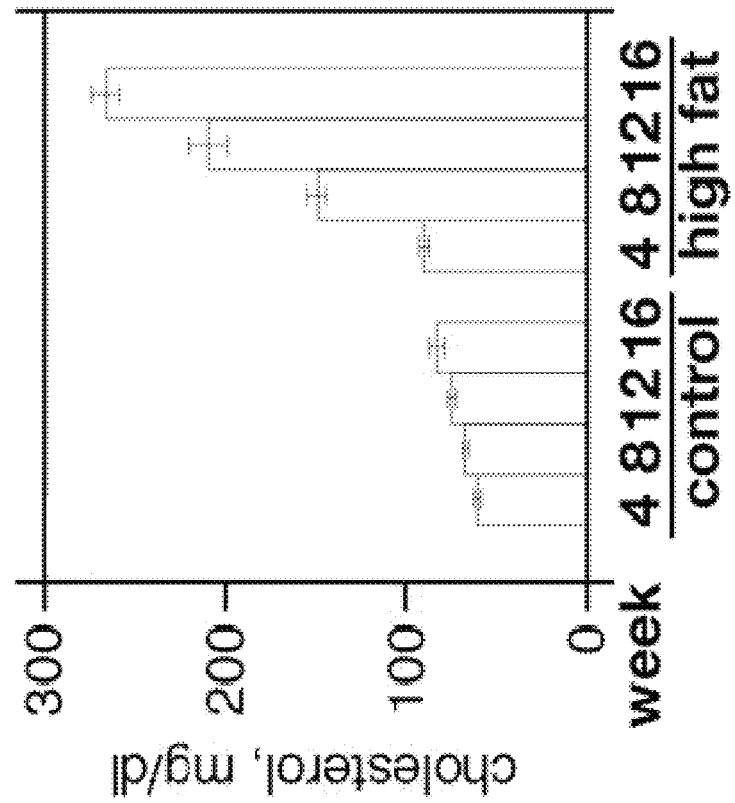

FIG. 16 depicts the total cholesterol level in serum was elevated in mice fed a high fat diet (detailed in Experimental Methods and Protocols). In this experiment, total cholesterol level in serum was quantitated in mice with both normal (7% fat) and high fat diets (21% fats). The average total cholesterol levels in normal diet fed mice were: week 4: 63+4 (mg/dl); week 8: 67+5 (mg/dl); week 12: 75+4 (mg/dl); and week 16: 80+6 (mg/dl). The average total cholesterol levels mice fed a diet high in fat were: week 4: 80+3 (mg/dl); week 8: 150+7 (mg/dl); week 12: 209+10 (mg/dl); and week 16: 266+12 (mg/dl). Graph represents mean±s.e.m, n=5.

Figure 17:
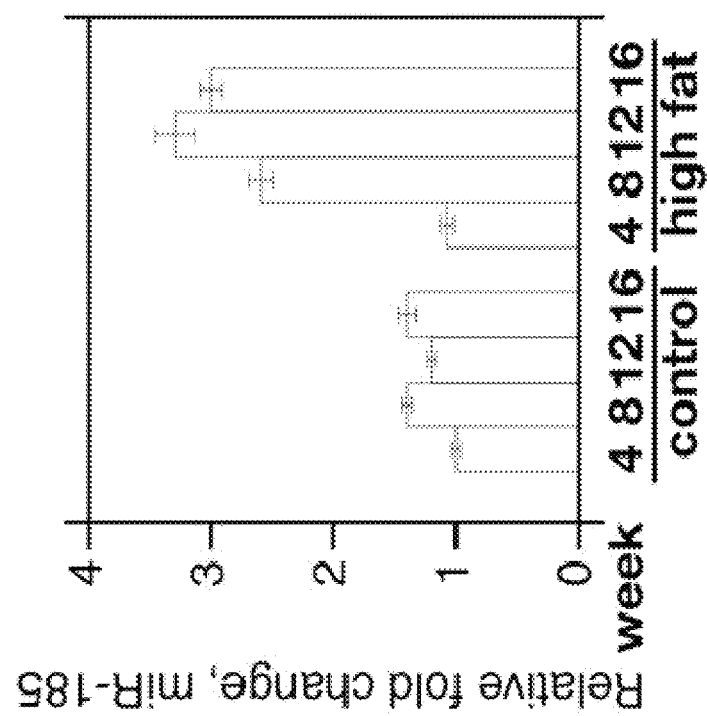

FIG. 17 depicts the up-regulation of miR-185 expression in vivo by cholesterol. In this experiment, the relative mature miR-185 expression was quantified by qRT-PCR in the liver of mice fed with both normal and high fat diets (21% fat) for 4, 8, 12 and 16 weeks. SNORD66 was used as internal control. Graph represents mean±s.e.m, n=5.

Figure 18A:
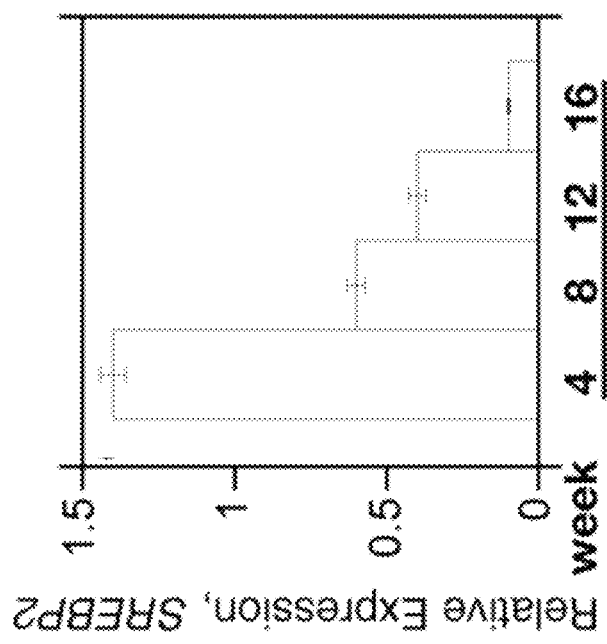
Figure 18B:
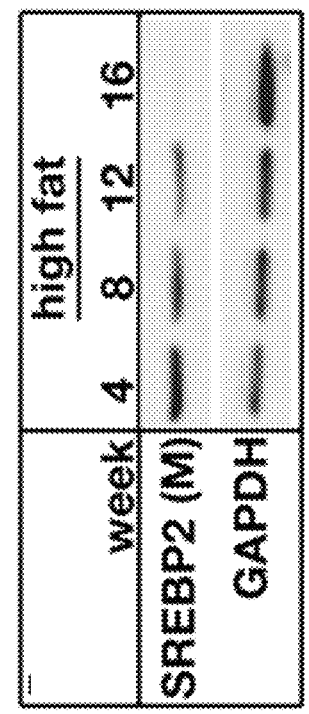

FIGS. 18A and 18B depict SREBP-2 expression in vivo is negatively regulated by cholesterol. FIG. 18A depicts the relative SREBP-2 mRNA expression in determined the liver of mice fed a high fat diet for 4, 8, 12 and 16 weeks by qRT-PCR. FIG. 18B depicts a Western blot of mature (NT) SREBP-2 protein level in the liver of mice fed a high fat diet for 4, 8, 12 and 16 weeks by qRT-PCR. Graph represents mean ±s.e.m, n=5. GAPDH was used as internal control for both SREBP-2 mRNA and SREBP-2 protein.

Figure 19:
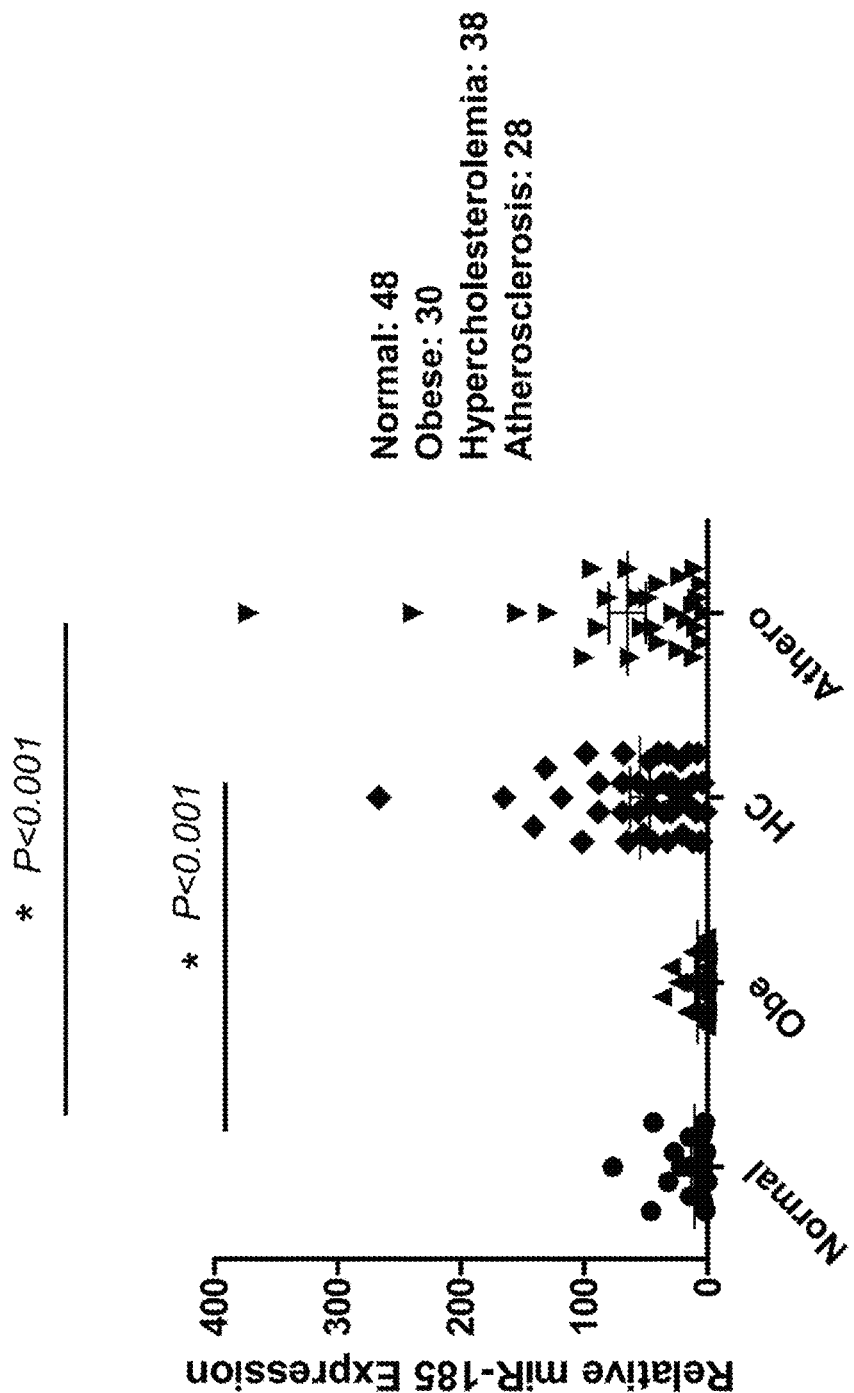

FIG. 19 depicts elevated levels of miR-185 in human serum samples with hypercholesterolemia and atherosclerosis. Mature miR-185 expression levels were examined in human serum samples under the following conditions: normal (48 samples); obese (30 samples); hypercholesterolemia (38 samples); and atherosclerosis (28 samples). RNU6-2 was used as an internal control. Graph represents mean±s.e.m. (*Significant as compared to controls ($P<0.001$)).

Figure 20A:
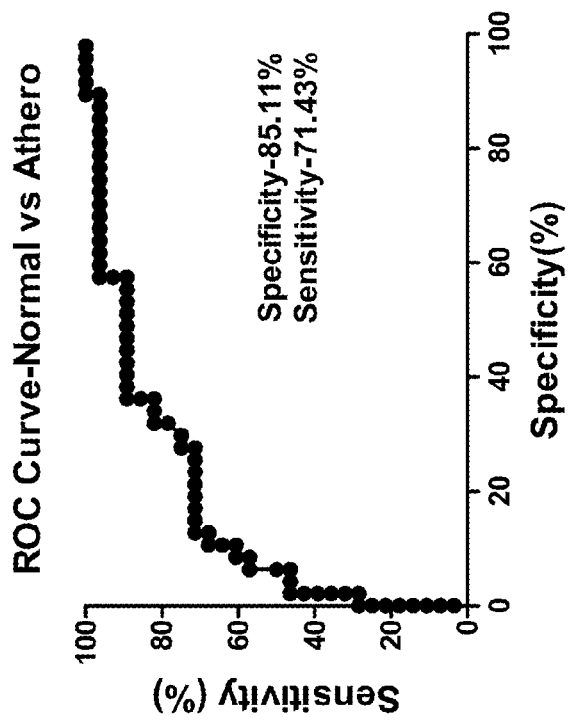
Figure 20B:
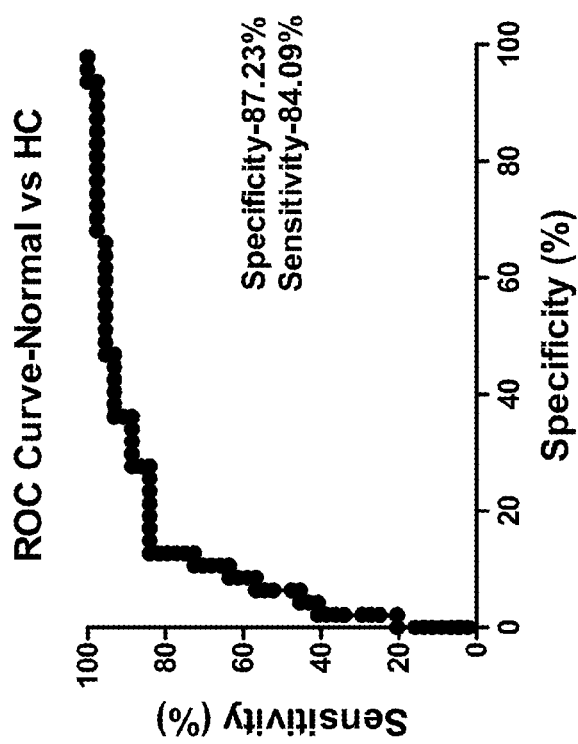

FIGS. 20A and 20B depict a receiver operating characteristic (ROC curve) analysis using miR-185 serum to discriminate healthy controls from hypercholesterolemia patients and atherosclerosis patients. FIG. 20A depicts an AUC yield (the area under the ROC curve) of 0.88 having a specificity of 87.23% and a sensitivity of 84.09% when discriminating hypercholesterolemia patients from healthy controls. FIG. 20B depicts an AUC yield (the area under the ROC curve) of 0.84 with a specificity of 85.11% and a sensitivity of 71.43% when discriminating atherosclerosis patients from healthy controls.

Figure 21:
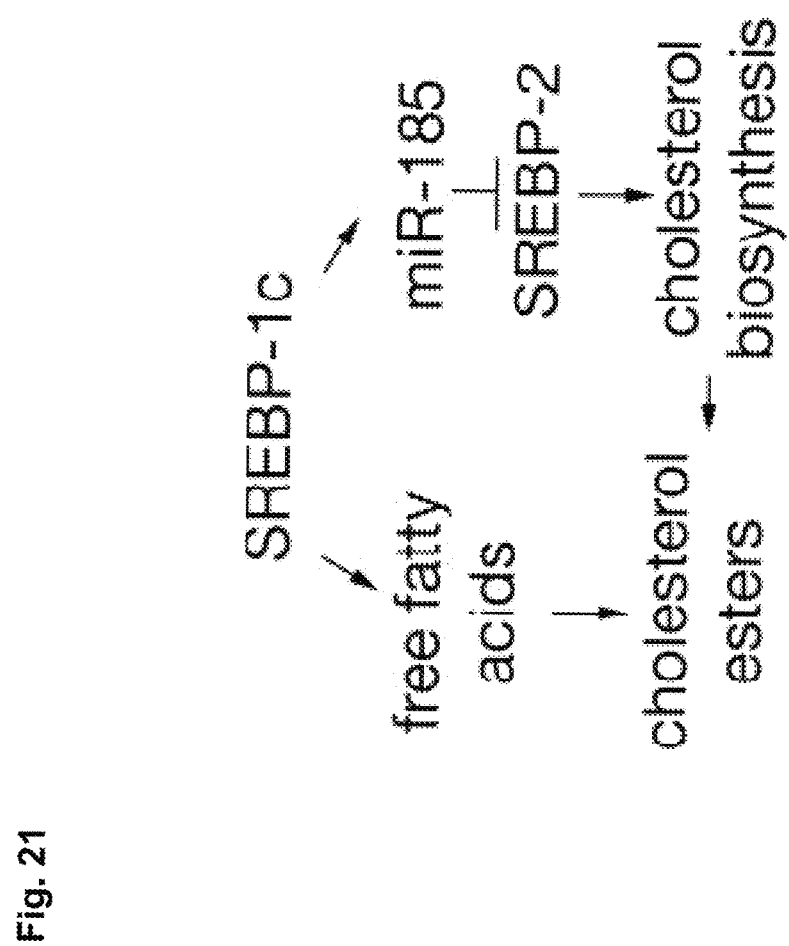

FIG. 21 depicts a schematic hypothesis of SREBP-1c/miR-185 feedback loop to ensure ratio of free cholesterol/cholesterol esters.

DETAILED DESCRIPTION OF THE INVENTION

The present invention can be better understood from the following description of preferred embodiments, taken in conjunction with the accompanying drawings. It should be apparent to those skilled in the art that the described embodiments of the present invention provided herein are merely exemplary and illustrative and not limiting.

Definitions:

Various terms used in this specification shall have the definitions set out herein.

As used herein, the term "microRNA" (miRNA) refers to a short ribonucleic acid (RNA) approximately 18-30 nucleotides in length (preferably 18-24 nucleotides, more preferably 22 nucleotides) that regulates a target messenger RNA (mRNA) transcript post-transcriptionally through binding to the complementary sequences on the target mRNA and results in the degradation of the target mRNA.

As used herein, the term "control miRNA" (miRcon) refers to a scrambled, non-targeting RNA sequence that serves as control transfection for miRNA.

As used herein, the term "control pre-miRNA" (miRcon) refers to a scrambled, non-targeting RNA sequence that serves as control transfection for miRNA. Transfection of control pre-miR-185 will not go into the RISC and process into a mature microRNA.

As used herein, the term "antagomiR" refers to a short RNA sequence that it contains the anti-sense sequence to miRNA. By base-pairing, antagomiR inhibits miRNA function.

As used herein, the terms "MicroRNA Response Elements" or "MREs" refer to the binding location of microRNA to 3' UTR region of a targeted mRNA (7-8 nucleotides) (seeding region) via complementary binding.

As used herein, the term "3'UTR" refers to 3'untranslated region of a particular mRNA. 3'UTR starts immediately after the stop codon of the coding region.

As used herein, the term "HepG2" refers to a human hepatocarcinoma cell line; "THLE-2" refers to an immortalized human liver cell line; "293T cells" refers to a human embryonic kidney cell line.

As used herein, the term "SREBP-2 "full length" (FL)" refers to the full length, unprocessed SREBP-2 protein. "N-terminal" (NT) represents the cleaved form of SREBP-2 protein by site 1 protease and site 2 protease. SREBP-2 NT is a mature form of SREBP-2 and functions as a transcriptional factor. The SREBP-2 gene (that encodes the SREBP-2 protein) in human has a nucleotide sequence set forth in GenBank Accession no. NM_004599, the content of which is incorporated herein by reference.

As used herein, the term "FDFT1" refers to the coding gene for squalene synthase protein.

As used herein, the term "methyl-β-cyclodextrin" (MCD) refers to a chemical compound that removes (depletes) cellular cholesterol content.

As used herein, the term "quantitative real-time PCR" (qRT-PCR) is synonymous with real-time polymerase chain reaction. A Real-time PCR is a method for detecting and quantitating an amplified PCR product based on a fluorescent reporter dye. The fluorescent signal increases in direct proportion to the amount of PCR product produced and is monitored at each cycle (in 'real time'), such that the cycle (C) at which the fluorescence first exceeds the detection threshold (t) correlates with the initial amount of target template. The term "$C_t$" refers to the reaction cycle at which the fluorescence exceeds the detection threshold is called the cycle threshold.

As used herein, the term "primer" refers to a strand of nucleic acids that serves as a starting point for DNA synthesis.

As used herein, the term "ROC" refers to "receiver operating characteristic." The ROC is a graphical plot of the sensitivity versus specificity (i.e., a graphical plot to reveal true positive rate versus false positive rate. The ROC is also represented by plotting the fraction of true positives out of the positives (TPR=true positive rate), versus the fraction of false positives out of the negatives (FPR=false positive rate), routinely denoted as a percentage. The ROC is used to determine the sensitivity and specificity of an assay (test) that may predict whether or not a patient suffers from a particular disease.

As used herein, the term "A," "T," "C", "G" and "U" refer to adenine, thymine, cytosine, guanine, uracil as a nucleotide base, respectively.

As used herein, the term "obese", when used in a human, refers to the accumulation of excess body fat in the human in an amount resulting in the body mass index (BMI) of a patient to exceed 30 kg/m$^2$.

As used herein, the term "hypercholesterolemia" refers to the presence of high levels of cholesterol in the blood. Hypercholesterolemia is diagnosed by assessing the lipid profile of a patient, which measures total plasma cholesterol, high density lipoprotein (HDL), very low density lipoprotein (VLDL), low density lipoprotein (LDL) and triglycerides. For purposes of this application, total cholesterol level exceeding 240 mg/dL or higher is considered to be hypercholesterolemia.

As used here, the term "atherosclerosis" refers to a disease condition in which an artery wall thickens as a result of the accumulation of fatty materials such as cholesterol and triglyceride. Accumulation of cholesterol and triglyceride occurs in tissue macrophages and promoted by low-density lipoproteins (LDL, plasma proteins that carry cholesterol and triglycerides) without adequate removal of fats and cholesterol from the macrophages by functional high-density lipoproteins (HDL). Clinical diagnosis of atherosclerosis includes angiography, and to a lesser extent "stress testing." Other diagnostic methods include anatomical detection, such as coronary calcium scoring by CT, carotid IMT (intimal media thickness) measurement by ultrasound, and intravascular ultrasound. Physiologic measurements such as lipoprotein subclass analysis, HbA1c, hs-CRP and homocysteine are also used in aiding the diagnosis.

As used herein, the term "SNORD66" refers to a non-coding RNA molecule used as internal control of microRNA expression.

As used herein, the term "RNU6-2" (U6 small nuclear 2 RNA) represents an internal control for microRNA expression.

As used herein, the terms "low density lipoprotein" or "LDL" refer to one of the five major groups of lipoproteins, which enable transport of multiple different fat molecules, as well as cholesterol, within the water around cells and within the water-based bloodstream. LDL contains a single apolipoprotein B-100 molecule and has a highly hydrophobic core consisting of polyunsaturated fatty acid, known as linoleate, and about 1500 esterified cholesterol molecules.

As used herein, the terms "low density lipoprotein receptor" or "LDLR" refer to a cell-surface receptor (discovered by Brown and Goldstein in 1985) that mediates the endocytosis of cholesterol-rich LDL by recognizing the apoprotein B100 that is embedded in the phospholipid outer layer of LDL particles. In humans, the LDL receptor protein is encoded by the LDLR gene. The LDLR gene in human has a nucleotide sequence set forth in GenBank Accession no. NM_000527, the content of which is incorporated herein by reference.

As used herein, the term "HMG-CoA reductase" or "HMGCR" refer to the rate-limiting enzyme of the mevalonate pathway, the metabolic pathway that produces cholesterol and other isopernoids. The HMGCR in human has a nucleotide set forth in GenBank Accession no. NM_000859, the content of which is incorporated herein by reference.

The present invention provides a novel approach of enhancing a miRNA in a cell, thereby reducing the LDL/cholesterol accumulation in the cell. Specifically, the present invention provides a method of enhancing miR-185 expression in a cell. The present inventors discovered that enhancing miR-185 reduces the expression of SREBP-2 mRNA and the protein thereof. The reduced SREBP-2 expression imparts a decrease in the expression of several SREBP-2 dependent genes required for de novo cholesterol biosynthesis and LDLR level in cells. The decreased SREBP-2 expression (due to an increased miR-185 in the cell) leads to: (i) inhibition of HMGCR, (ii) inhibition of squalene synthase, and (iii) reduced expression of LDLR, thereby causing a reduction in LDL and cholesterol accumulation.

The miR-185 gene in human is located at 22q11.21 and has a transcription start site (TSS) 17,088 bp from the miR-185 transcript. The nucleotide sequence of human miR-185 is set forth in accession number MI0000482, the content of which is incorporated herein by reference.

Expression of miRs in a cell is regulated by miRNA genes transcribed by either RNA polymerase II or RNA polymerase III into primary microRNA (pri-miRNA) (Filipowicz, et al., 2008 and Winter, et al., 2009). Pri-miRNAs are endonucleolytically cleaved by the nuclear microprocessor complex formed by the RNase III enzyme Drosha (RNA-SEN) and the DGCR8 (DiG'eorge critical region 8) protein to form a short stem-loop structure called precursor miRNA (i.e., pre-miR). The precursor miRNA usually consists of a ~70-100 nucleotide RNA transcript. The mature miRNA consists of a ~18-24 nucleotide RNA molecule.

In human, the nucleotide sequence of miR-185 precursor (pre-miR-185) is AGGGGGCGAGGGAUUGGAGA-GAAAGGCAGUUCCUGAUGGUCCCCUCCCCA GGGGCUGGCUUUCCUCUGGUCCUUCCCUCCCA (SEQ ID NO: 1). For purposes of this application, the term "precursor microRNA" or "pre-miR" refers to the short stem loop structures for miR after primary microRNA processing.

Pre-miRs are processed by Dicer (an endoribonuclease in the RNase III family that cleaves double-stranded RNA (dsRNA) into short double-stranded RNA fragments about 20-25 base pairs long, with a two-base overhang on the 3' end), producing the functioning mature microRNA (Filipo-wicz, et al., 2008; Winter, et al., 2009). In human, the nucleotide sequence of mature miR-185 is UGGAGA-GAAAGGCAGUUCCUGA (SEQ ID NO: 2). For purposes of this application, the term "miRNA" encompasses the precursor (unprocessed) or mature (processed) RNA transcript from a miR gene. The conversion of precursor miRNA to mature miRNA is aided by RNAse such as Dicer, Argo-naut, or RNAse III. In additional to the mature miRNA molecule obtained from the miRNA precursor through natural processing routes (e.g., cell lysates), chemical synthesis may be employed.

Mature miRNA is a single-stranded non-coding RNA consisting of about 18-24 nucleotides (an average of 22 nucleotides) and acts in the cytoplasm of a cell to cause a decrease in the expression of their cognate target messenger RNAs or translation of the mRNA's protein product. Without wishing to be bound by a theory, it is believed that miRNAs regulate gene expression in two ways. First, miR-NAs that bind to protein-coding mRNA sequences that are exactly complementary to the miRNA induce the RNA-mediated interference (RNAi) pathway. Messenger RNA targets are cleaved by ribonucleases in the RISC complex. The mature miRNA (typically about 22 nucleotide in length) enters the RNA Induced Silencing Complex (i.e., RISC) and binds to targeted messenger RNA (mRNA) by complimentary base-pairing, and results in translational repression or target degradation and gene silencing (e.g., SREBP-2). Second miRNAs that bind to imperfect complementary sites on messenger RNA transcripts, direct gene regulation at the posttranscriptional level but do not cleave their mRNA targets.

In one aspect, there is provided a method of transfection to enhance the expression of miR-185 in a cell. Various methodologies of enhancing the expression of miR-185 are provided. In one embodiment, the method involves trans-fecting into a cell a pre-miR-185 (i.e., precursor of miR-185). An exemplary pre-miR-185 is provided by SEQ ID NO: 1.

Transfection of genetic materials (e.g., pre-miR-185, miR mimic and the like) into mammalian cells (e.g., liver cells, vascular smooth muscle cells, etc) typically involves opening transientpores or 'holes' in the cell plasma membrane, to allow the uptake of genetic materials such as miRNAs. Transfection protocols are known in the art, including but not limited to electroporation, DEAE-dextran, calcium phosphate, liposomes (e.g., cationic lipids) and the like. For example, a direct approach to transfection is the gene gun, where the miRNAs is coupled to a nanoparticle of an inert solid (commonly gold) that is "shot" directly into the target cell's nucleus. The miRNA can also be introduced into cells using suitable plasmid as a carrier. Exemplary transfection includes, but not limited to, nucleofection, electroporation, heat shock, magnetofection, cationic liposome (e.g., proprietary transfection reagents such as Lipofectamine®, Dojindo® Hilymax, DreamFect™), nonliposomal lipid (e.g., Effectene®, FuGENE®), linear polyethylenimines (e.g., jetPEI®), and the like.

Using the transfection methodology, one skilled in the art may use a miR-185 mimic (in lieu of pre-miR-185) in order to enhance the expression of miR-185. For purposes of this application, a miR-185 mimic functions equivalently to enhance miR-185 expression by working in a similar fashion. It is intended that miR-185 mimic is encompassed in the same scope of pre-mir-185 invention. An exemplary miR-185 is commercially available from Life Technology (Grand Island, N.Y.; catalog no. MC 12486).

In one embodiment, transfection protocol utilizes calcium phosphate that involves mixing a HEPES-buffered saline solution containing phosphate ions with calcium chloride to form a fine precipitate with the positively charged calcium and the negatively charged phosphate. The formed precipitate, when added to cells, enhances the miRNAs to enter into cells.

In another embodiment, transfection is achieved using liposomes that function to fuse with the cell membrane and release the miRNAs into the cell. For mammalian cells, lipid-cation based transfection is typically used, because the cells are more sensitive. Other suitable transfection protocols may be used. For example, the use of cationic polymers such as DEAE-dextran or polyethylenimine. The negatively charge miRNAs binds to the polycation and the complex is taken up by the cell via endocytosis.

Transfection of genetic materials (e.g., miRNAs) may also use a virus vector. This method of over-expressing miR-185 may be achieved via stable transfection. In one embodiment, a viral vector (e.g. adenoviral vector, lentiviral vector and the like) may be conveniently used to carry (i.e., host) a pre-miR-185 (e.g., SEQ ID NO: 1). The expressing plasmid hosting the pre-miR-185 is delivered to cells via transfection or viral infection. Adeno-associated viruses (AAV) are currently in use for several clinical trials including Duchenne's muscular dystrophy (NCT00428935), Pompe Disease (NCT00976352) and Parkinson's Disease (NCT00643890), and can be adapted for use in the present invention. A lentiviral vector may be used to host the pri-miR-185 prior to its delivery to cells via transfection or viral infection. In a particular example, the pri-miR-185 (SEQ ID NO: 16) is cloned into SparQ Dual promoter lentivector (System Biosciences (Moutain View, Calif., catalog number: QM511B-1)) via PCR and restriction enzyme sites EcoRI and BamHI. The primers for PCR include: Forward: GAATTCCGCCCAGATCAAGATATGGT (SEQ ID NO: 17) and Reverse: GGATCCTGCACGCCCAGCT-GCT (SEQ ID NO: 18). The SparQ Dual promoter lentivector contains a CMV promoter for pri-miR-185 transcription. The SparQ-pri-miR-185 lentivector generates lentivirus for infection in cells (e.g., HepG2). Using this approach, a stable HepG2 cell line has been established that stably over-expressing miR-185.

In another embodiment, the DNA encoding miR-185 is contained in a suitable vector such as a plasmid, cosmid or phagemid through the use of pre-miR-185. Knowledge of miRNA genes also permits modification of cells to enhance the expression of an endogenous miR (e.g., miR-185). Cells can be modified (e.g., by homologous recombination) to provide increased miRNA expression by replacing, in whole or in part, the naturally occurring promoter with all or part of a heterologous promoter so that the cells express the miRNA at higher levels. The heterologous promoter may be inserted in such a manner that it is operatively linked to the desired miRNA encoding sequences (e.g., WO 94/12650, WO 92/20808, or WO 91/09955), the entire disclosures of these references are incorporated herein by reference. Cells may also be engineered to express an endogenous gene comprising the miRNA under the control of inducible regulatory elements, in which case the regulatory sequences of the endogenous gene may be replaced by homologous recombination. For example, gene activation techniques are described, for example, in U.S. Pat. Nos. 5,272,071 and 5,578,461, the entire disclosures of these references are incorporated herein by reference.

Without wishing to be bound by a theory, it is believed that the formation of the double-stranded RNA through the binding of the miRNA-185 triggers the degradation of the SREBP-2 mRNA transcript through a process similar to RNA interference (RNAi). The exact mechanism by which target genes are down-regulated is unclear. The human genome encodes over 1,000 miRNAs, which may target about 60% of mammalian genes. Pre-miR-185 is believed to enter the miRNA pathway and acts as the mature miRNA species. For purposes of this application, the pre-miR-185 (i.e., SEQ ID NO: 1) is intended to encompass the structurally similar or slightly modified miR-185 precursors (e.g., differ in one or a few nucleotides) as long as they function similarly to down-regulate the SREBP-2 mRNA transcript. Sequences complementarity in the 6-8 base pair 'seed regions' at the end of the miRNA-mRNA heteroduplex determines the specificity of miRNA-target RNA interactions.

In another aspect, the present invention provides that increasing miR-185 (i.e., enhancing miR-185 expression) in a cell that would target the SREBP-2 mRNA 3'UTR, thus repressing mRNA and protein expression levels of SREBP-2. The present inventors demonstrate that over-expression of miR-185 has a significant impact on the cholesterol metabolic pathway and LDL uptake as it regulates SREBP-2 dependent gene expression, thus regulating the mRNA transcription of the HMGCR, FDFT1, and LDLR genes. Thus, over-expression of miR-185 reduces the ability of cells to uptake LDL through repressing LDLR expression as well as inhibiting cholesterol synthesis and accumulation.

In a further aspect, the present invention provides a novel means of regulating SREBP-2 by transfecting a cell with a miR-185 precursor. A reduction in the expression of SREBP-2 protein levels can be achieved by transfecting the cells with miRNA-185 precursor so that the mature miRNA-185 binds with the 3'-UTR of SREBP-2 mRNA to reduce the expression of SREBP-2. The miRNA merely needs to include the matching "seed region" to effectively bind with the 3'-UTR of SREBP-2 mRNA. Preferably, the miRNA is up-regulated or over-expressed to increase the reduction in SREBP-2 expression levels. The level of miRNA-185 is up-regulated by a synthesized miRNA precursor, which enters the miRNA pathway and acts as a mature miRNA-185. An exemplary miRNA-185 precursor includes, for example, SEQ ID NO: 1.

In one aspect, the present invention provides a novel means of over-expressing miR-185 so as to reduce LDL accumulation in vascular cells and inhibit atherosclerosis by blocking intracellular cholesterol biosynthesis and reducing LDL uptake during foam cell formation from macrophage cells.

Accordingly, there is provided herein a method of elevating the expression level of miR-185 so as to inhibit the key cholesterol synthesis enzymes such as HMG-CoA reductase and squalene synthase as well as reducing the expression of LDLR and LDL uptake in vascular cells.

The present inventors observed that miR-185 regulates SBEBP-2. This finding is unexpected. The mechanisms that govern the activity of SBEBP-2 as a transcription factor are crucial in regulating SBEBP-2 dependent gene expression. This includes the expression HMG-CoA reductase, squalene synthase and LDLR. In the present study, our data suggest that miR-185 changes with high cholesterol and its expression may in turn regulate SBEBP-2 and further modulate the SBEBP-2 dependent gene expression.

SREBP-2 is a master switch regulating the transcription of an array of genes that are critical for maintaining intracellular cholesterol homeostasis. The present inventors discovered a novel molecular mechanism mediating SREBP-2 expression and function that will help better understanding of the complex systems of cholesterol metabolism. The novel molecular mechanism reveals that SREBP-2 expression is post-transcriptionally repressed by miR-185. By decreasing SREBP-2 expression level, miR-185 negatively regulates SREBP-2-dependent gene expression, resulting in a decrease in the expression of several genes required for de novo cholesterol biosynthesis, and a reduction in LDLR protein and LDL uptake. Strikingly, miR-185 expression is regulated by SREBP-1c, thus setting up a possible cholesterol/cholesterol ester-responsive feedback loop.

The present invention provides the functional miRNA-185 binding sites in the 3'-UTR of SREBP-2, which lead to down regulation of SREBP-2 gene expression, thereby down-regulate HMGCR, LDLR and FDFT1 gene expression. The use of miRNA-185 provides a novel therapy for treating cells that have high lipid or cholesterol accumulation and diseases characterized by high lipid or cholesterol accumulation.

The present invention satisfies the long-felt needs by providing a method of treating cells or a mammal suffering from high lipid or cholesterol accumulation in cells by reducing the expression of SREBP-2 protein levels in human liver cells or vascular cells. In one embodiment, the present invention provides a treatment therapy for using miR-185 to treat or attenuate a cell suffering from high lipid or cholesterol accumulation. In particular, the cells are transfected with miRNA-185 precursor, which down-regulates the expression of SREBP-2. In one particular embodiment, SREBP-2 protein expression levels in cells expressing high LDL or cholesterol accumulation can be reduced by transfecting the cells with miRNA-185 precursor so that the miRNA-185 binds with the 3'-UTR of SREBP-2 mRNA to reduce the expression of SREBP-2.

In one particular embodiment, miRNA-185 is up-regulated by the administration of miRNA-185 precursor alone or in combination with other cholesterol reducing agent. Non-limiting examples of cholesterol reducing agents include atorvastatin (Lipitor), fluvastatin (Lescol), lovastatin (Mevacor), pravastatin (Pravachol), rosuvastatin (Crestor), and simvastatin (Zocor).

In certain embodiments, non-limiting examples of cells include, for example, liver cells (i.e., hepatocytes), vascular smooth muscle cells, macrophages, and the like. These cells in obese individuals (having high LDL and cholesterol levels) can be treated by reducing the expression of SREBP-2 in the lipid laden cells by transfecting the cells with miRNA-185 precursor.

In one aspect, the present invention provides that a mammal suffering from high lipid or cholesterol accumulation can be treated by down-regulating SREBP-2 gene expression in cells. In various embodiments, the down-regulation of SREBP-2 gene expression is accompanied by the up-regulation of HMGCR, LDLR and FDFT1 gene expression in the cells. As such, the miRNA-185 indirectly down-regulates HMGCR, LDLR and FDFT1 genes by binding with SREBP-2, which negatively regulates these genes. The regulation of each can be achieved by transfecting the cells with a miRNA-185 precursor.

In another aspect, the invention provides a pharmaceutical formulation adapted for administering miRNA-185 precursor to a mammal (such as a human) in a therapeutically effective amount so that cells that have high accumulation of lipid or cholesterol can be transfected with miRNA precursor. The composition may conveniently include a pharmaceutically acceptable carrier. According to various embodiments, the present invention provides suitable formulations for administration of miRNAs. For instance, a formulation according to embodiments of the present invention can be provided in the form of a tablet, capsule or liquid preparation for oral administration. Most preferably, however, the formulation is provided as a liquid preparation for intravenous injection.

In other embodiments, the formulation can be provided in a form for injection or infusion. In general, methods of administering nucleic acids are well known in the art. For example, various formulations according to the present invention can be administered intravenously intramuscularly, subcutaneously and the like. The administration of these formulations translationally represses the expression of SRBEP-2, down-regulates HMGCR, LDLR and FDFT1 gene and their corresponding proteins, and thus regulates reduction of lipid or cholesterol in hepatocytes and vascular cells. Such administration routes and appropriate formulations are generally known to those skilled in the art.

For purposes of this application, "therapeutically effective amount" refers to the amount of miRNA-185 precursor to a mammalian cell or a mammal (e.g., human) having high lipid or cholesterol accumulation effective to treat, attenuate or prevent one or more targeted disorders. Therapeutically effective amount is the amount that is able to treat one or more symptoms of the disease, reverse the progression of one or more symptoms of high lipid/cholesterol related diseases (e.g., atherosclerosis) or halt the progression of one or more symptoms, or prevent the occurrence of one or more symptoms in a subject. The actual effective amounts of drug can vary according to the specific drug or combination thereof being utilized, its particular formulation, the mode of administration, and the age, weight, condition of the patient, and severity of the symptoms or condition being treated. One skilled in the art would be conveniently determine or optimize a daily therapeutic amount of the miRNA-185 precursor for the treatment.

The compositions described herein can be administered in effective dosages alone or in combination with other therapies, such as a cholesterol reducing agent (e.g., atorvastatin, fluvastatin, lovastatin, pitavastatin, pravastatin, rosuvastatin, simvastatin and the like) to provide a beneficial effect, for example reducing lipid and cholesterol accumulation or otherwise improving at least one symptom or manifestation of the disease. Alternatively, or in addition, the compositions described herein can be administered in effective dosages in combination with at least one other agent.

The present inventors examined the 500 bp upstream from miR-185 TSS in order to study miR-185 promoter activity. Within the 500 bp, it was discovered that there are two putative sterol response elements (SRE). Using this promoter construct, it was discovered that SREBP-1c can regulate miR-185, possibly through transcriptional regulation within the miR-185 promoter. miRs are transcribed from locations throughout the genome within the introns and exons of protein-coding genes, as well as intergenic regions. miRs are found to be transcriptionally regulated by changes in their promoter activity.

In one aspect, the present invention provides a novel approach to utilize miR-185 expression to regulate SREBP-dependent cholesterol biosynthesis, lending credence to the use of miR-185 treatment as a therapeutic application. The present study shows that miR-185 expression is regulated by the SREBP-1c transcription factor, through it binding to miR-185 promoter. These surprising results provide a novel mechanism by which SREBP-2 expression is regulated by its own SREBP family member SREBP-1c.

In one embodiment, the present invention provides an in vivo mouse model study that shows that miR-185 expression is elevated in mice having a high blood cholesterol level and reduced SREBP-2 protein. The observation in mice is observed in human where sera from individuals with high cholesterol show elevation of miR-185 expression. The present invention provides a novel regulatory axis for the post-transcriptional regulation of SREBP-2 expression, whose activity responds to, and is regulated by, cholesterol level.

The present invention points to a novel miR regulation in cholesterol metabolism. Several miRs have been suggested in initiation or progression of cardiometabolic disease (Fernandez-Hernando, et al., 2011 and 2013). Among the most studied miRs, miR-122 was the first reported miR associated with the regulation of cholesterol homeostasis in liver. The exact target genes regulated by miR-122, and the mechanism by which miR-122 regulates cholesterol level, remains to be fully elucidated. Another group of miRs includes the miR-33a/b family, which is found within the introns of SREBP-1 and SREBP-2. miR-33a/b have several targets that include the ATP binding-cassette (ABC) A1 cholesterol efflux pump, inhibiting its expression, which results in increased intracellular cholesterol concentration under conditions of need. Study reveals that miR-33a/b negatively regulate AMPK, a kinase that has been shown to phosphorylate and inhibit SREBP-2 activity. Thus, miR-33a/b expression would presumably up regulate SREBP-2 and cholesterol biosynthesis. The present invention is distinct apart from these previous studies in that this is the first report pointing to a novel mechanism by which miR-185 is up regulated through regulation by SREBP-1c. The miR-185 then targets SREBP-2, shutting it down, most likely ensuring that SREBP-2 does not increase cholesterol to a toxic level. In one embodiment the present invention provides that miR-185 level is up-regulated in mice fed a high fat diet and in human sera from patients with high cholesterol. It seems that in vivo, miR-185 regulates SREBP-2 activity when cholesterol level is high in order to precisely regulate the level of this lipid.

The present inventors have discovered that miR-185 acts as an inhibitor of SREBP-2 signaling in mammalian cells and, in particular, can reduce the expression of HMG-CoA, LDLR, and FDTI expression. Significant up-regulation of miR-185 was observed in mammalian cell culture, as well as in rodent models of high fat diet. Forced expression of the mature miR-185 (SEQ ID NO: 2) in mammalian cells significantly reduced the expression of SREBP-2 at both the transcriptional and translational levels. Accordingly, treatment with miR-185 holds clinical promise as a therapeutic molecule in the treatment and prevention of atherosclerosis. Up-regulating miR-185 directly or providing analogous pharmaceutical compounds exogenously that increase miR-185 levels should provide an effective therapy for atherosclerosis.

In addition to miR-185 having a direct effect on key transcripts regulating cholesterol synthesis, it has also been shown that miR-19b can exert indirect inhibitory actions on LDL uptake. For instance, increased miR-185 expression was observed to significantly decrease LDLR mRNA and protein levels which are necessary to suppress the LDL uptake in mammalian cells. miR-185 is thus a critical regulator of LDLR mediated LDL uptake in cells.

The present bioinformatic searches indicate there are several miR-185 microRNA response elements (MREs) present in the 3'UTR region of SREBP-2. The present study confirms the interaction of miR-185 with these MREs and their function in regulating SREBP-2 transcription. In situation with cholesterol depletion (by removal of intracellular cholesterol by MCD), we observed an acute activation of SREBP-2 and sterol gene expression, which is quickly blunted by over-expression of miR-185, suggesting that miR-185 regulation of SREBP-2 transcription may be fast and adaptable. Thus, tight transcriptional regulation of miR-185 expression is necessary under conditions where cholesterol level changes are drastic, such as times of fasting or after a high fat meal.

It is noteworthy that SREBP-1c expression is not regulated by cholesterol level, thus its constitutive presence would ensure a direct rapid regulation of miR-185 expression. As SREBP-1c function decreases, so should miR-185 expression, resulting in a fine-tuning in cholesterol level by the tuning on and off of SREBP-2 function. The loss of SREBP-1c function in this scenario presumes that there is some type of modification, either changes in expression, or some type of post-translational modification. Thus, the three components in this loop need to be regulated by the same sensing mechanism.

The present invention provides a molecular basis by which miR-185 is up-regulated by a transcription factor (i.e., SREBP-1c (Invitrogen, catalog no. 4390824)) and that miR-185 is involved in fatty acid synthesis. Without wishing to be bound by a theory, it is speculated that miR-185 inhibits SREBP-2 expression, thus reducing de novo cholesterol biosynthesis and LDL uptake. SREBP-1c expression is activated by a number of metabolic states, and through LXRα activation by oxysterols. This latter activation is believed to be required for the production of the fatty acids needed for cholesterol ester synthesis. Based on our observation, it is reasonable to believe the SREBP-1c/miR-185 feedback loop ensures that the ratio of free cholesterol/cholesterol esters is maintained. Inhibition of SREBP-2 function by miR-185 would result in a decrease in cholesterol level, allowing for the conversion of the remaining intracellular pool to non-toxic cholesterol esters. As the level of free fatty acids increase, SREBP-1c expression would decrease, miR-185 expression would be blunted, and SREBP-2 expression would increase. This would allow for the synthesis of the cholesterol needed to reduce the free fatty acid pool through esterification. In mice fed a high fat diet, we observed that as cholesterol level rose, miR-185 also increased, while SREBP-2 protein decreased. It is known that the expression of SREBP-1c is negatively regulated by an increase in polyunsaturated fatty acids, thus providing support to our proposed model.

Little is known about the transcriptional regulation of miRs. Our findings show that through binding to a specific SRE within the promoter region of miR-185, SREBP-1c transcriptionally activated miR-185 expression, resulting in the suppression of SREBP-2-dependent events. Moreover, knockdown of SREBP-1c actually resulted in increased SREBP-2 expression and protein. Thus, SREBP-1c inversely regulated SREBP-2 expression. The present invention identifies the promoter regions of miRs that regulate transcription, and elucidating the transcription factors binding to these sites, thus allow for their manipulation as a potential therapy for attenuating cholesterol-related diseases.

In one embodiment, the present invention provides a basis for why SREBP-1$^{-/-}$ mice show an elevated SREBP-2 expression level in the liver. It is possible that a decrease in miR-185 expression due to reduced SREBP-1c expression results in elevated SREBP-2 expression, acting as a compensatory mechanism. This regulatory mechanism may be harmful to an individual's health status, as SREBP-1$^{-/-}$ mice have a 3-fold increase in cholesterol biosynthesis in the liver, and a 50% increase in hepatic cholesterol level. The present finding indicates that the regulation of miR-185 expression is specific to SREBP-1c, as siRNA against SREBP-2 had no effect. Unlike SREBP-1c, the SREBP-1a expression level is extremely low in liver cells, thus precluding its study.

In one aspect, the present invention provides a method to inhibit miR expression include using antisense oligonucleotides. Other suitable antisense oligonucleotides such as the various known chemically modified versions (e.g., 2'-O-methyl-group (OMe)-modified oligonucleotides, and locked nucleic acids (LNAs)) are contemplated to be included in the present invention. The present invention provides a unique miR-185 in the efficacy of miR therapy to treat diabetes conditions, liver disease, heart diseases. One of skilled in the art would, based on the present finding, develop an efficient delivery method to deliver miR-185 to effect an efficient miR treatment. A non-limiting example includes an adenovirus, nanoparticle, and micro-vesicular delivery systems. The present invention provides a method of overexpressing miR-185 to inhibit SREBP-2 activity and provides a feasible therapeutic for treating cholesterol-related diseases. The present invention also provides a method of enhancing miR-185 to regulate SREBP-2 and reduce LDLR expression, leading to increased LDL and free fatty acid levels.

Despite the knowledge that multiple miRNAs are present in eukaryotic cells, it remains a daunting task to identify specific miRNA species within the total miRNA pool, whose expression patterns associate or correlate with a particular disease such as lipid disorder or cardiovascular diseases. Detection of miRNA often faces further difficulties because expression levels vary among different sources of biological samples (e.g., tissues or blood).

In one aspect, the present invention provides a method of detecting miR-185 in a biological sample from a human subject. Biological sample refers to human serum. The present miRNA assay may be performed in other suitable biological samples such as blood, plasma, cells and the like. Serum can be derived from clotting the withdrawn blood (without use of anti-coagulants). Whole blood is obtained and blood cells (e.g., peripheral blood lymphocytes) can be isolated using standard techniques (e.g., Ficoll-Hypaque). A corresponding control serum sample can be obtained from a normal human individual or population of normal individuals. The control blood sample is processed along with the sample from the subject, so that the expression levels of miRNAs from the subject's sample can be compared to the corresponding miRNAs from the control's sample.

In a further aspect, the present invention is directed to the use of miR-185 as a biomarker for lipid/cholesterol related vascular diseases, particularly atherosclerosis. The present inventors have observed that patients who suffered from atherosclerosis exhibit a high level of miR-185 expression in comparison to normal healthy individuals. Accordingly, measurements of the level of miR-185 in blood can be used as a biomarker/indicator for atherosclerosis. Moreover, the presence of elevated levels of miR-185 in combination with an elevated level of cholesterol in blood (e.g., serum or plasma) serves as a biomarker/indicator for atherosclerosis.

In certain embodiments of the invention, the diagnosis or prognosis may be achieved by measuring the amount of miR-185 that is present at increased levels in the blood (e.g., serum or plasma) of a subject suspected of suffering from atherosclerosis. In some cases, the level of the miR-185 marker will be compared to a control to determine whether the level is increased. The control may be an external control, such as a miRNA in a blood (e.g., serum or plasma) sample from a subject known to be free of atherosclerosis. The external control may be a sample from a normal (non-diseased) subject. In other circumstances, the external control may be a miRNA from a non-blood sample like a tissue biopsy or a known amount of a synthetic RNA. The external control may be a pooled, average, or individual sample; it may be the same or different miRNA as one being measured. An internal control is a marker from the same sample being tested, such as a miRNA control.

The present inventors discovered a correlation between high cholesterol in humans and the expression of the specific miR-185. The present invention provides a method of detecting miR-185 in serum as a means of specifically predicting or detecting cardiovascular diseases associated with hypercholesteremia in humans. The miR-185 assay represents a useful and non-invasive diagnostic methodology wherein quantifying serum miR-185 as a biomarker in the diagnosis of cardiovascular diseases such as hypercholesterolemia and heart diseases such as atherosclerosis.

The present study establishes that serum expression of miR-185 is at a statistically distinct level in patients with high cholesterol and abnormal LDLR as compared to those in normal control subjects.

The present quantification assay for serum miRNA has a high sensitivity of 84.09% and specificity of 87.23%, which is suitable for commercial purposes. The serum expression of the disclosed miRNA therefore provides a practical utility tool as diagnostic markers in the diagnosis of lipid abnormality and heart diseases. The present invention therefore provides a simple, inexpensive, easy-to-use test for cardiologists to complement and extend existing diagnostic measures so as to improve patient treatment and outcome.

The present invention provides a method of quantifying or determining the expression level of miR-185. In one aspect, the present invention provides a method of predicting or diagnosing whether a human subject is at risk of having lipid disorder, LDLR abnormality or cardiovascular diseases. The method comprises quantifying the expression level of miR-185 in a biological sample (e.g., serum) from a human subject suspected of suffering from lipid disorder, LDLR abnormality or cardiovascular diseases and comparing the expression level of the miR-185 in normal control subjects. In one embodiment, the human subject has high cholesterol in serum or atherosclerosis.

In a clinical study, the present inventors discovered an elevated miR-185 in patients suffering from high cholesterol or atherosclerosis. It is discovered that patients suffering from cardiovascular diseases exhibit an increased expression level of miR-185 in serum. In one aspect, the present invention provides a method of utilizing the miR-185 of predicting or diagnosing whether a human subject has lipid disorder, cardiovascular disease, atherosclerosis, LDLR abnormality. The present invention provides a method of predicting if a human subject having a cardiovascular disease when the human subject has an increase in miR-185.

The relative miRNA gene expression in the control and normal samples is determined with respect to one or more miRNA expression standards. The standards can comprise, for example, a baseline miRNA gene expression level, the miRNA gene expression level in a standard cell line, the miRNA gene expression level in unaffected tissues of the subject, or the average level of miRNA gene expression previously obtained for a population of normal human controls. Expression level of specific miRNA standards is used as a reference (i.e., normalizer), and exemplary normalizer includes miR-155, RNU6-2 and the like.

The expression level of a miRNA in a biological sample is measured or quantified using any suitable technique for detecting RNA expression levels in a biological sample. Suitable techniques (e.g., qRT-PCR) for determining miRNA expression level in a biological sample are encompassed in this invention. In one embodiment, the expression level of a miRNA is detected or quantified by using qRT-PCR. In another embodiment, the expression level of miRNA may be detected or quantified using Northern blot analysis. To determine or quantify the expression level, total cellular RNA is isolated from biological sample using nucleic acid extraction reagents, followed by centrifugation. All the nucleic acids are prepared by precipitation and DNA is removed by treatment with DNase and precipitation. The RNA molecules are then separated by gel electrophoresis on agarose gels according to standard techniques, and transferred to nitrocellulose filters. Detection and quantification of specific miRNA is performed using hybridization. (e.g., Molecular Cloning: A Laboratory Manual, J. Sambrook et al., eds., 2nd edition, Cold Spring Harbor Laboratory Press, 1989, the entire disclosure of which is incorporated by reference).

After the miRNA expression level in a biological sample is determined or quantified, one skilled in the art would compare the expression levels of the miRNAs in the biological sample obtained from a subject suspected of suffering from a lipid disorder disease or cardiovascular disease with the expression levels of the miRNAs from control subjects. Such comparison would provide information regarding whether a particular miRNA undergoes up-regulation or down-regulation relative to a reference miRNA in each biological sample. Increased risk of atherosclerosis refers to an increase in the occurrence of atherosclerosis in individuals as compared to the occurrence of atherosclerosis in healthy individuals (e.g., cholesterol levels less 200 mg/dL or lower for a total count, LDL levels of less than 130 mg/dL or less, and triglyceride levels of 150 mg/mL or less or HDL levels of 60 mg/dL or higher). The identification of differential expression levels in the biological samples would permit the use of such information as a diagnostic and prognostic tool to predict or monitor lipid disorder or cardiovascular disease outcomes.

In another aspect, the present invention provides a method for characterizing atherosclerosis in a patient. In certain embodiments, the present method comprises measuring a level of miR-185 in a blood or tissue sample from the patient and determining whether the level of miR-185 in the sample is decreased or elevated as compared to a control sample. In certain embodiments, the blood sample is serum or plasma sample. In certain embodiments, the tissue sample is a liver biopsy. In other embodiments, the tissue sample is a vascular biopsy. In certain embodiments, the control sample is a corresponding blood or tissue sample from a patient that does not have atherosclerosis. In other embodiments, the method comprises the combined use of blood cholesterol and miR-185 levels to characterize the progression of atherosclerotic diseases.

In one embodiment, the present invention thus provides a kit, comprising a reagent (e.g., PCR primers and probes in a qRT-PCR) that specifically detect miR-185 in blood (e.g., plasma or serum) and an instruction thereof for use of said kit in a method according to the invention. The kit may optionally contain one or more controls and/or one or more standards.

The following examples are provided to further illustrate various preferred embodiments and techniques of the invention. It should be understood, however, that these examples do not limit the scope of the invention described in the claims. Many variations and modifications are intended to be within the spirit and scope of the invention.

EXPERIMENTAL STUDIES

Example 1 miR-185 Targets SREBP-2 mRNA 3'UTR and Leads to Repression of SREBP-2 mRNA Expression We conducted a bio-informatics search using the TargetScan6.1 and miRBase. Based on the search, we identified four (4) predicted microRNA response elements (MREs) present within the 3'UTR region of human SREBP-2 mRNA. The relative location of respective MREs is depicted in FIG. 1A. We asked which microRNA (miRNAs), if any, binds to these predicted MREs. Specifically, we examined a particular miR (i.e., miR-185) that may bind to these predicted MREs.

In this series of study, we used a luciferase reporter assay to monitor the potential binding of a miRNA to the predicted MREs. We transfected into HEK293 cells a pSwitchLight wide type (WT)-SREBP-2-3'UTR luciferase plasmid (which serves as a control). We also transfected into HEK293 cells with a mutant SREBP-2-3'UTR luciferase reporter. The luciferase report contained a mutant SREB-2-3'UTR that has either 2C or 3 C that have been mutated to G (i.e., point mutations) in the four (4) predicted MREs which are believed to be miR-185 seeding sites. FIG. 1B depicts the miR-185 seeding regions of the respective MREs, and the mutated sites are underlined and bold. The wild type SREBP-2 3'UTR has the nucleotide sequence set forth in SEQ ID NO: 3. The SREBP-2 3'UTR mutant has the nucleotide sequence set forth in SEQ ID NO: 4.

In short, the four (4) SREBP-2-3'UTR mutants included the following sites (details in FIG. 1B):
1) Site 1: CTCT(C→G)TCT(C→G)CCC;
2) Site 2: TCT(C→G)T(C→G)T(C→G)CTG;
3) Site 3: ACT(C→G)T(C→G)T(C→G)CTT; and
4) Site 4: ATT(C→G)T(C→G)T(C→G)CCT.

After transfection with the luciferase plasmids containing the wild type SREBP-2-3'UTR (SEQ ID NO: 3) and SREBP-2-3'UTR mutant (SEQ ID NO: 4), we then assayed for WT-SREBP-2-3'UTR luciferase activity in the presence of (i) miR-185, (ii) the mutated miR-185, and (iii) a control miR. Control miR was obtained from Ambion (catalog no. AM17110). The control miR sequence for transfection is random sequence Pre-miR™ molecule that we has been previously tested in human cell lines and validated to produce no identifiable effects on known miR function.

As shown in FIG. 2, transfection of pre-miR-185 (SEQ ID NO: 1) significantly decreased the luciferase activity in cells carrying a wild type SREBP-2 3'UTR reporter plasmid (70%; p<0.03), as compared to cells transfected with only a control miR. The addition of point mutations (via site-directed mutagenesis) within the four (4) MREs significantly interfered with miR-185 binding and silencing SREBP-2 3'UTR luciferase activity (FIG. 2, two right columns). These results indicate that miR-185 targets and interacts with the MREs present within the SREBP-2 mRNA 3'UTR.

Example 2 miR-185 Represses the Expression of SREBP-2 in Human Liver Cells

Figure 3B:
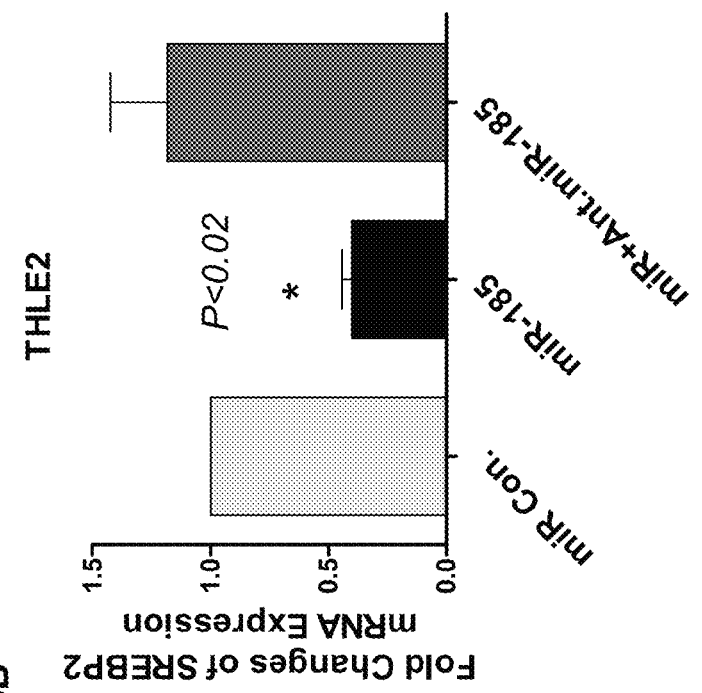
FIGS. 3A and 3B depict that miR-185 negatively regulates SREBP-2 mRNA expression in human liver cells.
Figure 3A:
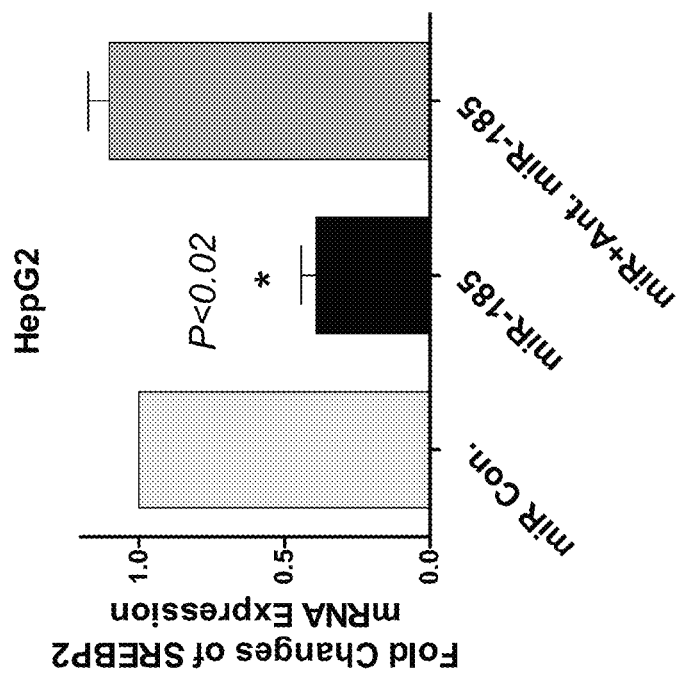

It is generally believed that miRNAs, by targeting mRNA 3'UTRs, can silence their target genes through initiating mRNA degradation or inhibition of translation. In this series of study, we determined if miR-185 would target the 3' UTR of the endogenous SREBP mRNA. First, we determined if overexpression of miR-185 may attenuate the expression of endogenous SREBP-2 mRNA. HepG2 (FIG. 3A) or THLE2 cells (FIG. 3B) were transfected with pre-miR-185 (SEQ ID NO: 1) or a control miR (described in Example 1) and SREBP-2 mRNA expression was determined by qRT-PCR.

Figure 4:
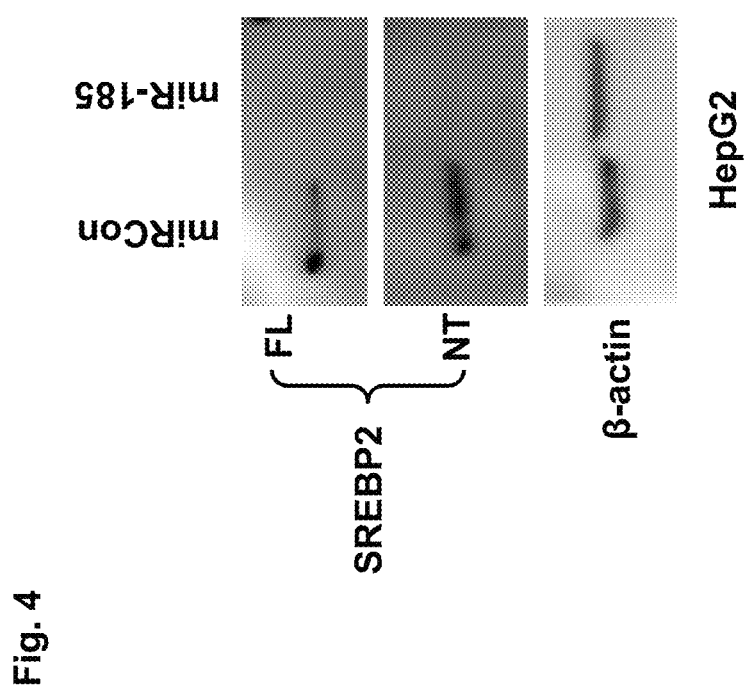
FIG. 4 depicts that miR-185 down-regulates SREBP-2 protein level in human liver cells (i.e., HepG2 cells). SREBP-2 protein level was determined by a Western blot of miR-185 over-expressing HepG2 cells and a control miR transfected HepG2 cells. A polyclonal antibody against (i.e., recognizes) the N-terminal of both the full length (FL) and activated N-terminal (NT) of SREBP-2 was seen to react in control conditions (bands at 120 kD and 60 kD), but disappeared in the miR-185 transfected cells, indicating the miR-185 over-expression down regulates SREBP-2 protein expression. β-actin was used as loading control.

Over-expression of miR-185 (by transfection with SEQ ID NO: 1) significantly decreased SREBP-2 mRNA level (~two-fold) in HepG2 and THLE-2 cells (FIG. 3A, FIG. 3B; p<0.02), as compared to miR-control expressing cells. Binding of miR-185 to the endogenous SREBP-2 3'UTR also reduced the level of SREBP-2 protein as evidenced by Western blot analysis (FIG. 4).

We used antagomiRs (anti-miRs) to block the binding of miR-185 to the MREs present within the SREBP-2 mRNA 3'UTR. Addition of an antagomiR to miR-185 (Invitrogen, CA, catalog no. AM 12486) together with miR-185 (i.e., miR+Ant. miR-185) abolished the miR-185 targeting of the SREBP-2 3'UTR (FIG. 3A, p>0.01), confirming specificity.

Altogether, the data demonstrates that miR-185 negatively regulates SREBP-2 expression by binding to the SREBP-2 mRNA 3'UTR region, which leads to reduced SREBP-2 mRNA and protein levels. We speculate that miR-185 plays an important role in regulating SREBP-2-dependent cholesterol biosynthesis.

Example 3 miR-185 Affects SREBP-2 Dependent Gene Expressions

SREBP-2 plays a pivotal role in regulating cholesterol biosynthesis, by controlling the expression of several important genes involved in de novo cholesterol metabolism including HMGCR (HMG-CoA reductase), farnesyl-diphosphate farnesyltransferase 1 (FDFT1; squalene synthase) and LDLR (low density lipoprotein receptor).

Figure 5A:
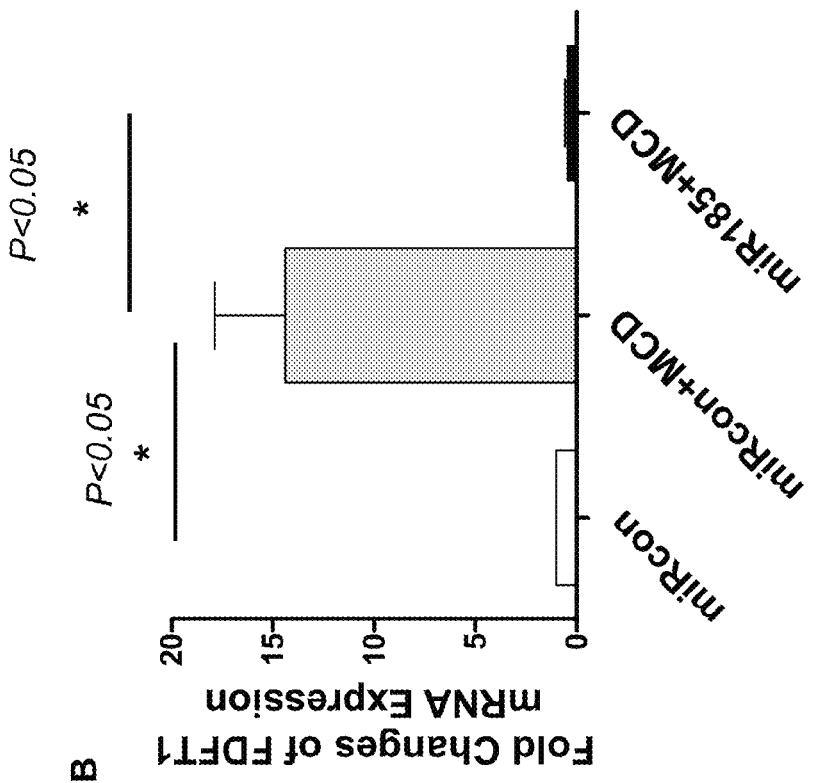
FIGS. 5A and 5B depict that miR-185 impacts SREBP-2 transcribed gene expressions.

In this series of study, we examined if miR-185 may affect in vivo SREBP-2-dependent gene expression, HepG2 cells were transfected with pre-miR-185 (SEQ ID NO: 1) and the expression basal level of FDFT1 was determined by qRT-PCR (See, Experimental Methods and Protocols). A control pre-miR was used to serve as a control. As shown in FIG. 5A, miR-185 over-expressing cells had a >2-fold decreased basal mRNA level of FDFT1 as compared to cells transfected with control miR (p<0.01).

SREBP-2 is activated when cell cholesterol levels decrease. It normally resides in the endoplasmic reticulum (ER) when cholesterol levels are high, but upon cholesterol depletion is transported to the Golgi complex, where it is cleaved into a soluble SREBP-2 transcription factor fragment by the SIP1/S2P proteases. This fragment translocates to the nucleus, where it binds sterol response elements (SREs) within genes required for de novo cholesterol biosynthesis. SREBP-2 binding to SREs results in gene upregulation.

Figure 5B:
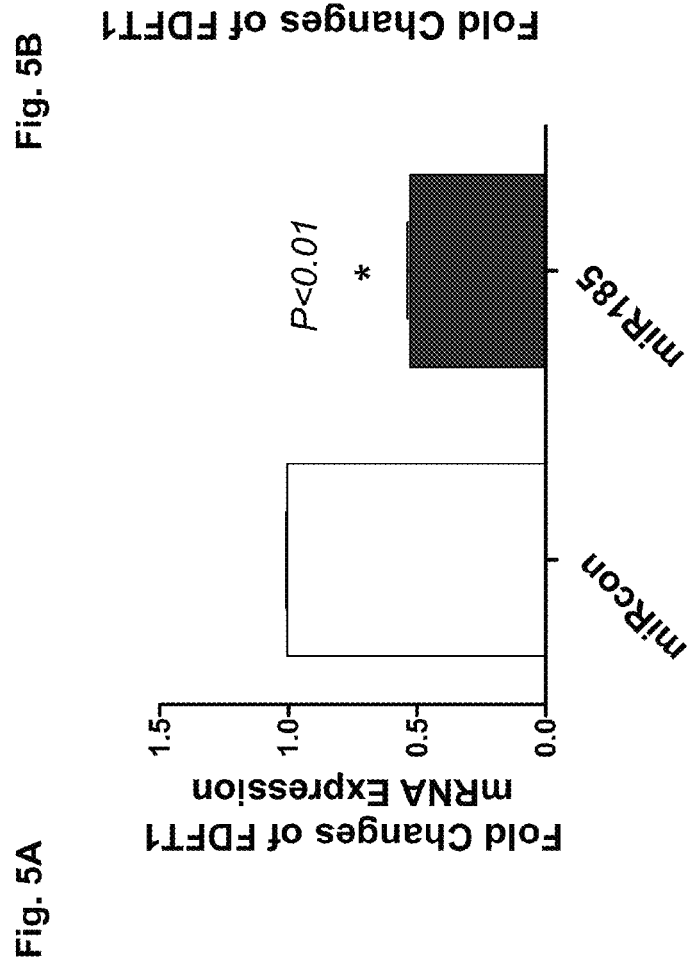

To explore if miR-185 regulates SREBP-2 mRNA level under conditions where SREBP-2 is activated by cholesterol depletion, we treated HepG2 cells expressing pre-miR-185 with the cholesterol-depleting agent, methyl-β-cyclodextrin (MCD). Treatment of cells with MCD resulted in cholesterol depletion. We then examined FDFT1 expression in the absence or presence of MCD. In the presence of a control pre-miR (Ambion, catalog no. AM17110), FDFT1 gene expression increased in the presence of MCD and cholesterol depletion (FIG. 5B, miRcon vs. miRcron+MCD). On the other hand, the expression of miR-185 abolished MCD-stimulated FDFT1 expression (FIG. 5B, miRcon+MCD vs. miR-185+MCD).

Figure 6A:
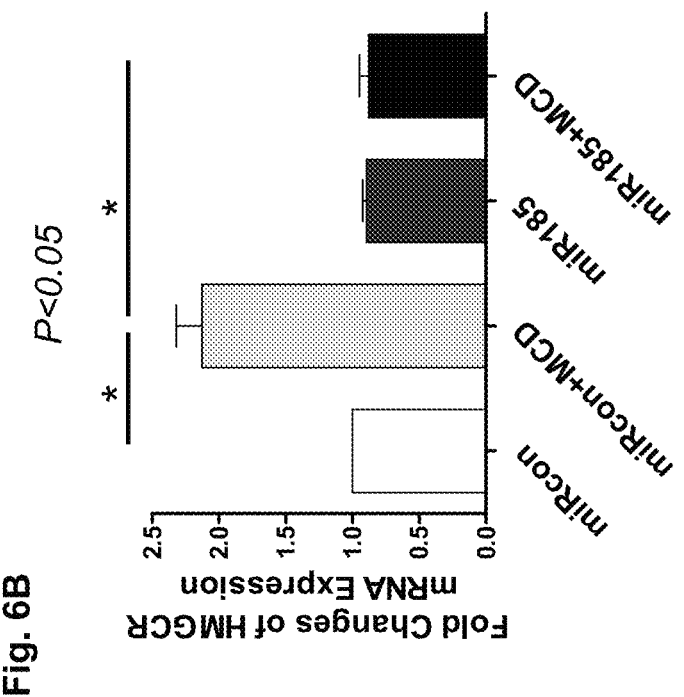
FIGS. 6A and 6B depict miR-185 mediating other SREBP-2 controlled gene transcriptions.
Figure 6B:
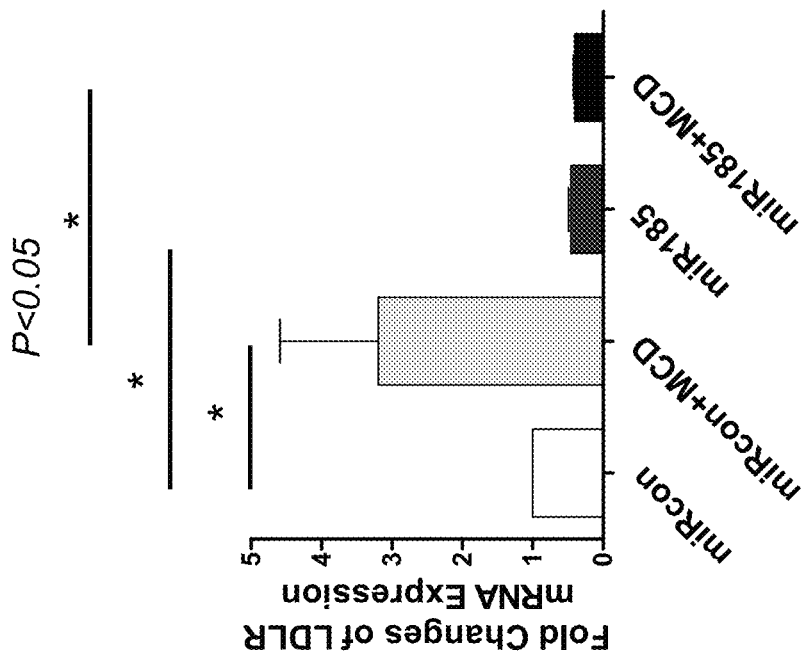

We obtained identical results when we examined the basal and MCD-stimulated levels of LDLR (FIG. 6A). Interestingly, the basal level of HMGCR did not significantly decrease in HepG2 cells overexpressing miR-185 (FIG. 5B, miRcon vs. miR-185). However, miR-185 overexpression abolished MCD-stimulated cholesterol depletion (FIG. 6B; miRcon+MCD vs. miR-185+MCD).

Altogether, the data indicate that miR-185 expression abolishes SREBP-2-dependent gene expression under conditions of cholesterol depletion. These results suggest that miR-185 plays a critical role in regulating de novo cholesterol biosynthesis.

Example 4 miR-185 Reduces LDLR Protein and Decreases LDL Uptake In Human Cells and Attenuates HMGCR Activity LDL receptor (LDLR) is known to play an important role in LDL uptake by internalizing LDL-cholesterol via endocytosis. In order to explore the physiological significance of miR-185-dependent regulation of SREBP-2 expression, we examined the level of LDLR protein by western analysis, used immunofluorescence to examine the level of endogenous LDLR in cells, and determined cellular LDL uptake using the fluorescently-labeled LDL, LDL-BODIPY.

Figure 7A:
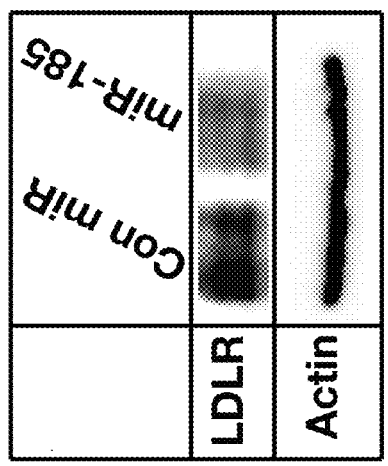
FIGS. 7A and 7B depict the reduction of LDLR total protein level and cell surface expression by miR-185 over-expression.
Figure 7B:
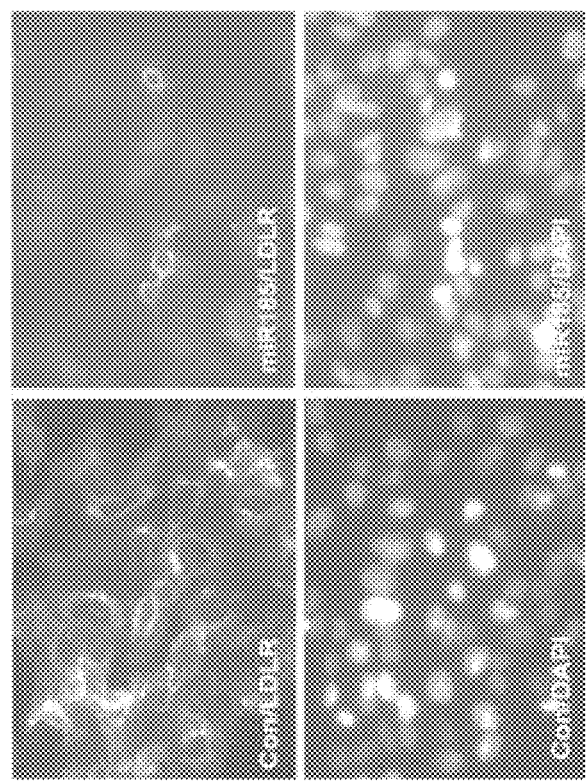

As shown in FIG. 7A, we found that LDLR protein level was decreased in HepG2 cells overexpressing pre-miR-185 as compared to miR control cells. Moreover, the endogenous level of LDLR was drastically reduced in these cells (FIG. 7B; Con/LDLR vs. miR185/LDLR).

Figure 8:
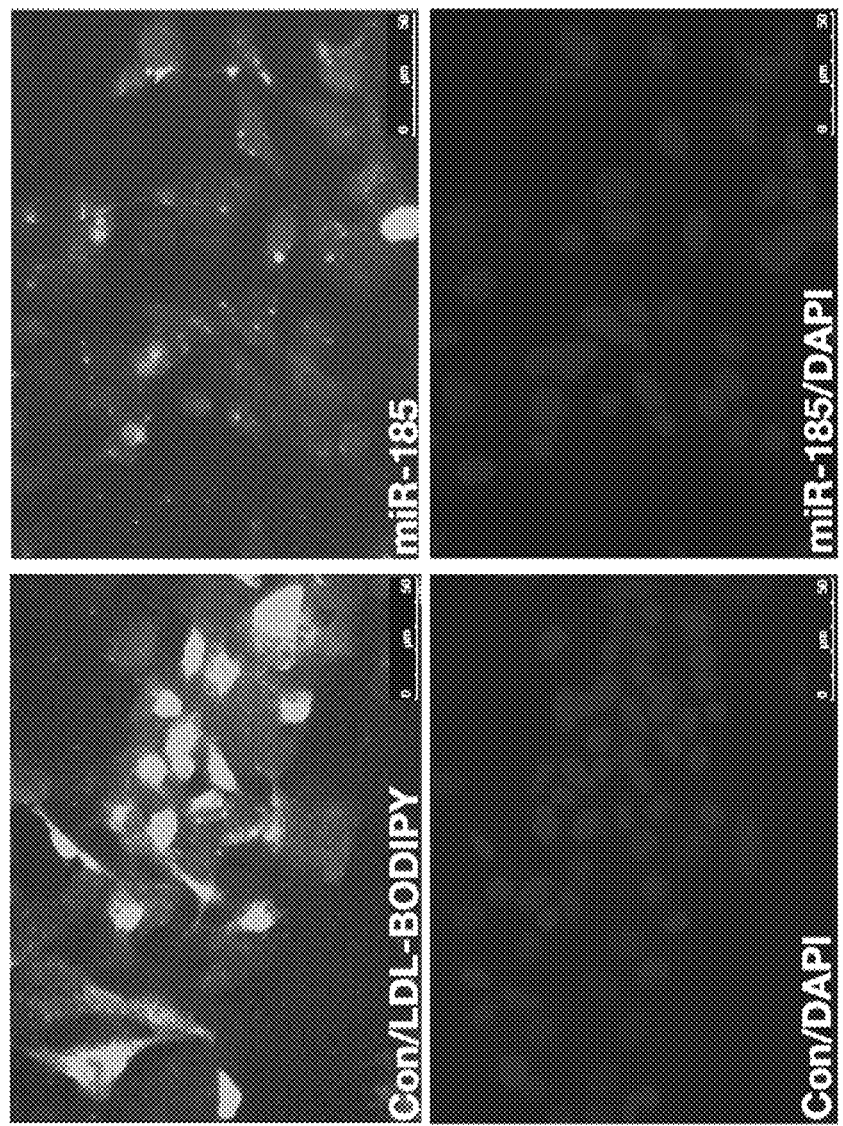
FIG. 8 depicts the loss of LDLR impairs LDL influx in miR-185 over-expressing HepG2 cells. Uptake of LDL by HepG2 cells was observed by incubating control miR or pre-miR-185 transfected HepG2 cells with LDL-BODIPY (5 µg/ml). DAPI was used to counter stain nuclei. Leica DMI6000 fluorescent microscopy was used to visualize the staining.

As shown in FIG. 8, the level of internalized LDL-BODIPY was severely reduced in miR-185 expressing cells (FIG. 8; Con/LDL-BODIPY vs. miR-185). Altogether, these results indicate that miR-185 reduces intracellular cholesterol level by reducing the uptake of cholesterol via decreased LDLR. SREBP-2-dependent events are attenuated by miR-185 binding to the 3'UTR of the mRNA of SREBP-2, which causes a reduction in SREBP-2-dependent expression of HMGCR, FDFT1, and LDLR, which causes reductions in cholesterol synthesis and uptake.

Figure 9:
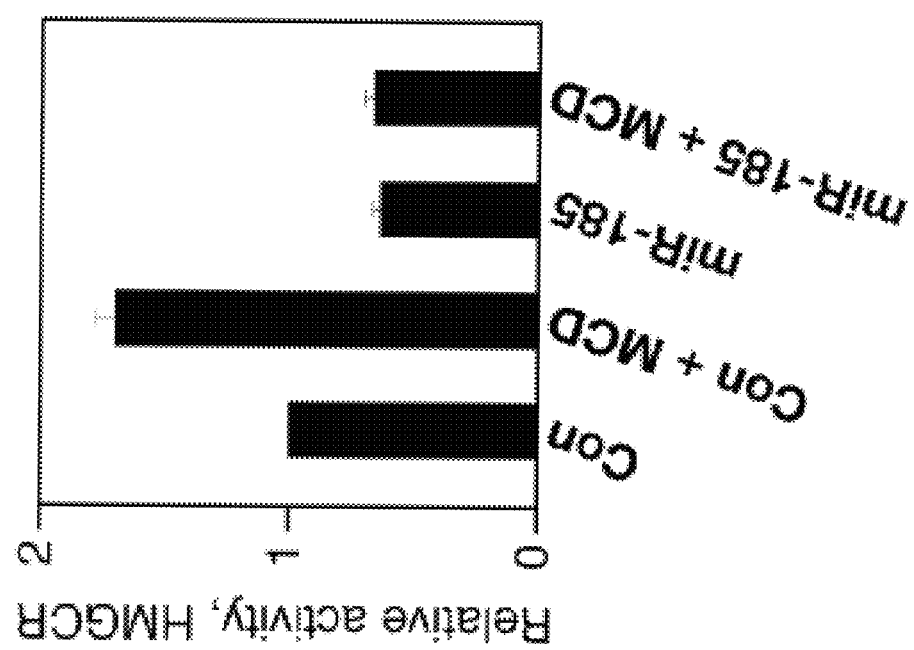
FIG. 9 depicts miR-185 over-expression decreased HMGCR activity in HepG2 cells. The HMGCR activity was quantitated by normalizing the isolated [$^{14}$C]-mevalonolactone to internal control [$^{3}$H]-mevalonolactone. The labeled mevalonolactone was separated from non-reacted HMG-CoA by column chromatography using AGp1-X-8 resin. The same amount of [$^{3}$H]-mevalonolactone was added into the reaction serving as internal control. The relative activity was calculated by normalizing the HMGCR activity in the miR-185 over-expressing, MCD treated control and miR-185 over-expressing HepG2 cells to control HepG2 cells. Graph represents mean±s.e.m. from three independent experiments. (*Significant as compared to controls (P<0.001)).

HMGCR is the rate-limiting enzyme of de novo cholesterol biosynthesis and converts HMG-CoA to mevalonate. As demonstrated above, miR-185 inhibited MCD-induced HMGCR transcription through SREBP-2 expression repression (FIG. 6B). To determine the physiological significance of this repression, HMGCR activity was determined in HepG2 cells overexpressing miR-185. In the presence of MCD there was a 1.75-fold increase in HMGCR activity over baseline (FIG. 9, con vs. con+MCD, P<0.01). This increase was abolished when miR-185 was overexpressed (FIG. 9, con+MCD vs. miR-185+MCD). Interestingly, the expression of miR-185 alone decreased HMGCR activity (FIG. 9, con vs. miR-185), although it did not reduce HMGCR expression (FIG. 6B).

Example 5 miR-185 Expression Is Decreased By Cholesterol Depletion

Figure 10:
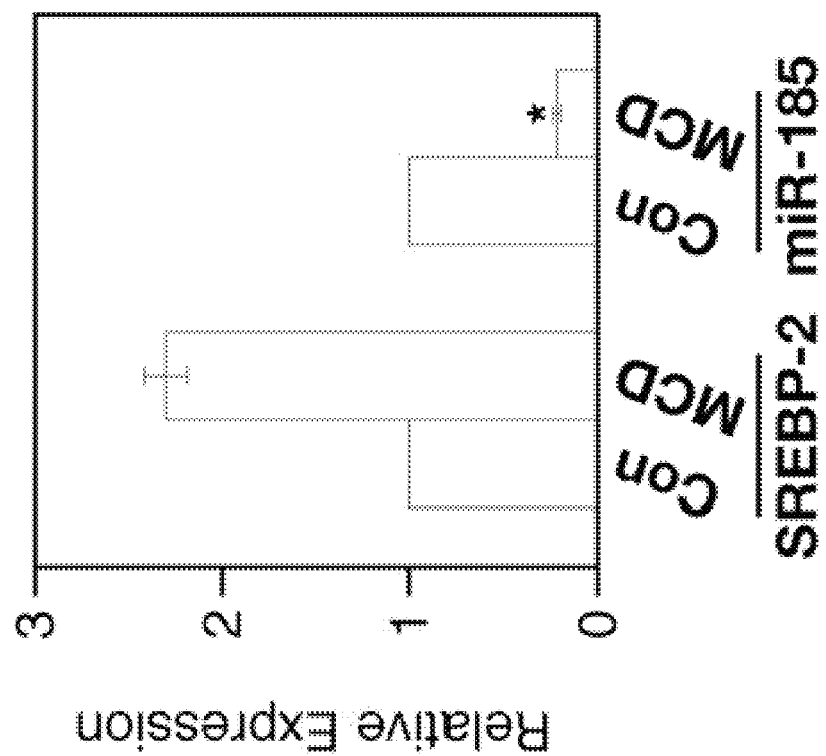
FIG. 10 depicts intracellular cholesterol depletion in human liver cells, up-regulates SREBP-2 via down-regulated miR-185. The relative mRNA expression of SREBP-2 and miR-185 were determined in HepG2 cells treated with MCD or dimethyl sulfoxide (DMSO) control by qRT-PCR. GAPDH and RNU6-2 were used as internal controls for SREBP-2 mRNA and miR-185 expressions, respectively. Bar graphs represent mean±s.e.m from three independent experiments. (*Significant as compared to controls (P<0.01)).

We next addressed whether miR-185 expression itself was regulated in response to cholesterol level. HepG2 cells were treated with and without MCD, and SREBP-2 and miR-185 expressions were determined. In the presence of MCD, SREBP-2 expression increased ~2.5-fold when compared to control cells (FIG. 10, con vs. MCD (SREBP-2), p<0.01), while miR-185 expression decreased ~80% under the same conditions (FIG. 10, Con vs. MCD (miR-185), p<0.01).

Example 6

Transcriptional Regulation of miR-185 By SREBP-1c

Transcriptional regulation of miRs is a main mechanism by which endogenous miR expression and function are regulated. In this series of study, we explored the transcriptional regulation of miR-185. We determined the transcriptional start site (TSS) of pre-miR-185 using miRStart (mirstart.mbc.nctu.edu.tw). We chose to examine 500 bp upstream of the TSS in order to study the miR-185 promoter activity.

Within this 500 bp, we identified two putative SREBP-1c binding sites (FIG. 11A, B). Based on the presence of these binding sites, we first examined if SREBP-1c regulated miR-185 promoter activity. We used a chromatin immunoprecipitation assay (ChIP) to determine if SREBP-1c binds the miR-185 promoter at SRE sites. SREBP-1c was observed to bind to the 500 bp fragment upstream of the miR-185 TSS (FIG. 11C).

Figure 12:
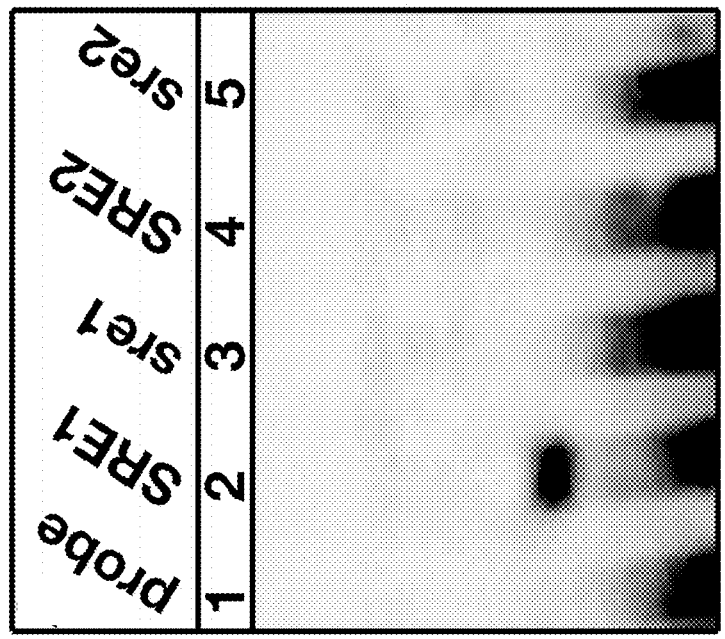
FIG. 12 depicts HepG2 nuclear proteins binding to SRE within the miR-185 promoter. HepG2 nuclear extract was incubated with the presence of: lane 1: free probe; lane 2.

Electrophoretic Mobility Shift Study: We employed an electrophoretic mobility shift assay to identify the binding site(s) for SREBP-1c. Only a mobility shift of the SRE1 probe was observed using nuclear extracts (NE) from HepG2 cells, when compared to SRE2 (FIG. 12, lane 2 vs 4). Binding was abolished when SRE1 was mutated (FIG. 12, lane 2 vs. lane 3), indicating specificity. A 20-fold cold competitor SRE1 probe also abolished binding (FIG. 13, lane 2 vs. 3).

In order to confirm that the protein-DNA complex formation was due to a SREBP-1c-SRE1 interaction, a gel-super shift assay was performed using anti-SREBP-1c polyclonal antibodies. Addition of this antibody to the nuclear extract resulted in a super shift in the protein-DNA complex (FIG. 13, lane 2 vs. lane 4). Thus, SREBP-1c binds to the SRE1 in the miR-185 promoter.

We next asked if SREBP-1c binding to the miR-185 promoter regulated miR-185 expression. We decreased the expression of SREBP-1 in HepG2 cells using siRNA to knock down SREBP-1c, and determined the effect on miR-185 expression using qRT-PCR. Knocking down the expression of SREBP-1c was accompanied with a concomitant decrease in SREBP-1c protein (FIG. 14A). More importantly, the level of mature miR-185 (SEQ ID NO: 2) was significantly decreased in siRNA SREBP-1 knocked down HepG2 (>2 fold, FIG. 14B; p<0.01) and THLE2 cells (>2 fold, FIG. 14C; p<0.01), as compared to control cells. Strikingly, we also found that the level of SREBP-2 mRNA expression (FIG. 15A) and protein (FIG. 15B) increased in cells with decreased SREBP-1 levels.

Based on these results, we concluded that: (1) an increase in miR-185 causes a decrease in SREBP-2 expression and protein, which causes a decrease in the expression of genes required for de novo cholesterol biosynthesis; and (2) the expression of miR-185 is regulated through a feedback mechanism involving SREBP-1c binding to SREs in the miR-185 promoter. We concluded that miR-185 plays a critical role in maintaining proper cholesterol homeostasis, through regulating the expression of SREBP-2 in response to changes in the level of cellular cholesterol.

Example 8

Increased miR-185 Expression Level Correlates With High Blood Cholesterol and Reduced SREBP-2 Protein in Mice Fed a High Fat Diet To determine the in vivo relevance of miR-185-dependent regulation of SREBP-2 expression, we monitored the miR-185 expression, and cholesterol and SREBP-2 levels, in mice fed a high fat atherogenic diet (21% fat) or a normal fat diet (7% fat). Mice (C57BL/6J) (B6) were fed respective diet for 16 weeks, and blood and organs were harvested at 4, 8, 12, and 16 weeks.

In mice fed a high fat diet, there was a time-dependent increase in blood cholesterol level, while control animals fed a normal diet did not show this increase (FIG. 16). The level of miR-185 also showed a time-dependent increase (FIG. 17), while SREBP-2 mRNA expression and protein level decreased in mouse liver (FIGS. 18A & B). Thus, the in vivo animal data confirm that was observed in in vitro study.

Example 9 miR-185 is Elevated in High Cholesterol Human Serum Samples

The detection of miRs in peripheral blood has recently been used as a biomarker for cancer diagnostics. However, the global profile of specific miRs expressed in correlation with associated metabolic disease states remains to be elucidated.

To begin to define this profile as it pertains to certain lipid-related diseases, we determined the level of mature miR-185 (SEQ ID NO: 2) level in human serum samples from patients with no disease, high cholesterol, and atherosclerosis. All disease state values were compared to the level of miR-185 in normal patient samples. As compared to normal serum, the relative mature miR-185 (SEQ ID NO: 2) level was elevated in sera from patients with hypercholesterolemia and atherosclerosis. The average sera level of miR-185 from obese patients was similar to that seen for normal patients (FIG. 19).

To further validate miR-185 as a potential diagnostic marker for hypercholesterolemia and atherosclerosis, we generated ROC curves (receiver operating characteristics) we first examined if the level of serum miR-185 could be used to discriminate hypercholesterolemia from healthy controls. An AUC (the areas under the ROC curve) of 0.88 was observed. At a cut-off value of 15.59, the specificity and sensitivity for this marker was 87.23% and 84.09%, respectively in discriminating those individuals with high cholesterol levels versus those with normal levels (FIG. 20A). The calculated AUC value for serum miR-185 for discriminating atherosclerosis patients from healthy controls was 0.84. At the cut-off value of 16.39, the specificity and sensitivity of this was 85.11% and 71.43%, respectively (FIG. 20B). These results suggest that miR-185 may serve as a novel biomarker for lipid-mediated diseases.

Experimental Methods and Protocols

1. Cell Lines and Human Serum Samples

THLE-2, HepG2 and 293T cells were obtained from ATCC. Normal, obese, hypercholesterolemic and atherosclerotic patient sera samples were obtained from Bioreclamation (Hicksville, N.Y.). All serum samples were from patients of an age >50 years old. Mixed sex and race samples were used. THLE-2 cells were cultured in BEGM medium (Lonza, Wakersville, Md., catalog no. CC3171) with supplements (Lonza Walkersville, Md., catalog no. CC3170) following the manufacturer's instruction. HepG2 cells were cultured in MEM medium (supplemented with 10% fetal bovine serum (Gibco, Life Technology, Grand Island, N.Y., catalog no. 16000044), 1% non-essential amino acid (Sigma, St. Louis, Mo., catalog no. M7145), 1% sodium pyruvate (Sigma, St. Louis, Mo., catalog no. 58636) and 1% L-glutamine (Sigma, St. Louis, Mo., catalog no. G7513). The MEM medium was obtained from Sigma, St. Louis, Mo., catalog no. 51411C. 293T cells were cultured in DMEM medium (supplemented with 10% fetal bovine serum, 1% L-glutamine) (Sigma, St. Louis, Mo., catalog number D5796). All cells were incubated at 37° C. and 5% $CO_2$. For methyl-β-cyclodextrin (MCD, Sigma, St. Louis, Mo., catalog number C4555) treatment, cells were incubated in serum free medium containing 50 mM MCD at 37° C. for 10 minutes.

2. RNA Isolation and Quantitative Real-Time PCR

Total RNA was extracted for mRNA analysis. In brief, total RNA was extracted with TRIzol reagent (Invitrogen, Life Technology, Grand Island, catalog no. 1559618). cDNA was synthesized from total RNA using $RT^2$ Easy First Strand Kit (Qiagen, Philadelphia, Pa., catalog no. 330421). qRT-PCR was carried out using a Stratagene MX3005P (Stratagene, Santa Clara, Calif.,) using primers for SREBP-2, LDLR, HMGCR, FDFT1 and GAPDH. The relative mRNA levels were normalized to levels of the GAPDH housekeeping gene. In addition, small RNA was converted to complimentary DNA from 100 ng (human serum) or 500 ng (cell lines) total RNA using the miScript II RT kit (Qiagen, Philadelphia, Pa., catalog no. 218160). Follow up miR analysis was performed by qRT-PCR using miScript SYBR Green PCR Kit (Qiagen, Philadelphia, Pa., catalog no. 218073) and miR specific (miR-185) primers (Qiagen, Philadelphia, Pa., catalog no. MS00001736) and normalizing to RNU6-2 (Qiagen, Philadelphia, Pa., catalog no. MS00033740) snRNA levels as a control.

qRT-PCR was performed following the below steps:
1. cDNA synthesis for mRNA quantitation (using $RT^2$ Easy First Strand Kit):
   1. Total RNA: 1.0 µg
   2. Buffer GE2 (gDNA elimination buffer): 6.0 µl
   3. RNase-free H2O to a final volume of: 14.0 µl 4. Incubate at 37° C. for 5 min, and immediately place on ice for at least 1 minute
5. Add 6 µl of the BC5 Reverse Transcriptase Mix to each 14-µl Genomic DNA Elimination Mixture for a final volume of: 20 µl
6. Incubate at 42° C. for exactly 15 min and then immediately stop the reaction by heating at 95° C. for 5 minutes
7. Hold the finished reaction on ice until ready to use for real-time PCR, or placed at −20° C. for long-term storage 2. cDNA synthesis for microRNA quantitation (using miScript II RT kit):
   1. 5× miScript HiSpec Buffer :4 µl
   2. 10× Nucleics Mix: 2 µl
   3. RNase-free water: Variable
   4. miScript Reverse Transcriptase Mix: 2 µl
   5. Template RNA: 100/500 ng
   6. Total volume: 20 µl
   7. Add template RNA to each tube containing reverse-transcription master mix
   8. Mix gently, briefly centrifuge, and then place on ice
   9. Incubate for 60 min at 37° C.
   10. Incubate for 5 min at 95° C. to inactivate miScript Reverse Transcriptase Mix and place on ice
   11. If you wish to proceed with real-time PCR immediately, dilute the reverse transcription reactions (1:5) with Nuclease free water or to be stored at −20° C.

3. SYBR Green qRT-PCR for mRNA:
   1. 2× SYBR Green PCR Master mix:12.5 µl
   2. Forward Primer: 0.2 µM
   3. Reverse Primer: 0.2 µM
   4. cDNA: 1 µl
   5. Nuclease free water: variable
   6. Total volume: 25 µl
   7. Mix the reaction mix thoroughly but gently, and dispense the reaction mix into each well of a 96-well plate
   8. The cycling conditions for real-time PCR:
      a. PCR Initial activation step: 15 min 95° C.
      b. 3-step cycling:
         i. Denaturation: 15 s 94° C.
         ii. Annealing: 30 s 55° C.
         iii. Extension: 30 s 70° C.
         iv. Perform fluorescence data collection
         v. Cycle number: 40 cycles 4. SYBR Green qRT-PCR for microRNA:
   1. 2× SYBR Green PCR Master mix: 12.5 µl
   2. 10× miScript Universal primer: 1 µl
   3. 10× miScript Primer Assay: 1 µl
   4. cDNA: 1 µl
   5. Nuclease free water: variable
   6. Total volume: 25 µl
   7. Mix the reaction mix thoroughly but gently, and dispense the reaction mix into each well of a 96-well plate.
   8. The cycling conditions for real-time PCR:
      a. PCR Initial activation step: 15 min 95° C.
      b. 3-step cycling:
         i. Denaturation: 15 s 94° C.
         ii. Annealing: 30 s 55° C.
         iii. Extension: 30 s 70° C.
         iv. Perform fluorescence data collection
         v. Cycle number: 40 cycles 3. Transfection and Luciferase Reporter Assay For human miR-185 over-expression, pre-miR-185 (Life Technology, Grand Island, N.Y., catalog no. 002271) was used. pLightswitch-SREBP-2 3'UTR luciferase reporter plasmid was obtained from Switchgeargenomics (Menlo Park, Calif., catalog no. S805826). 3'UTR mutant pLightswitch SREBP-2 reporter plasmid was generated with point mutations within miR-185 binding sites. The Quick Change lightning Mutagenesis kit (Stratagene, Santa Clara, Calif., catalog no. 210518) was used to construct SREBP-2 3'UTR mutant. The resulting mutant (SEQ ID NO: 4) contains two or three point mutations in each of the MRE sites: 1) CTCT(C to G) TCT(C to G)CCC; 2) TCT(C to G)T(C to G)T(C to G)CTG; 3) ACT(C to G)T(C to G)T(C to G)CTT; 4) ATT(C to G)T(C to G)T(C to G)CCT. The construct was confirmed by sequencing.

SREBP-1c siRNA (catalog no. 4390824) and control siRNA (catalog no. 4390843) were obtained from Thermo Scientific. HEK293T and THLE-2, HepG2 cells were transfected with pre-miR-185 (SEQ ID NO: 1), control pre-miR (Ambion, catalog no. AM17110), Lightswitch-SREBP-2 3'UTR reporter plasmid, Lightswitch-SREBP-2 3'UTR mutant plasmid, SREBP-1 siRNA, or control siRNA using Lipofectamine® 2000 (Invitrogen, Life Technology, catalog no. 11668019) following manufacturer's instructions.

The luciferase activity was detected using the Lightswitch Reporter Assay System (Switchgeargenomics, Menlo Park, Calif., catalog no. LS010) 24 hours after the transfection as described in manufacturer's instructions.

pSwitchLight WT-SREBP-2-3'UTR Luciferase plasmid (Switchgear Genomics, Menlo Park, Calif., catalog no. S805826), the WT SREBP-2 3'UTR luciferase plasmid is available from a commercial source. The mutant SREBP-2 3'UTR luciferase plasmid was obtained from WT SREBP-2 3'UTR luciferase plasmid by point mutation.

4. Western Blotting

Western blotting was performed using anti-SREBP-2 rabbit polyclonal antibody (Abcam, Cambridge, Mass., catalog no. ab30682), anti-SREBP-1c rabbit polyclonal antibody (Santa Cruz Biotechnology, Dallas, Tex., catalog no. sc-8924) and anti-LDLR rabbit polyclonal antibody (Abcam Cambridge, Mass. catalog no. ab30532). Anti-β-actin mouse monoclonal antibody (Abcam Cambridge, Mass., catalog number ab8226) was used as loading control. Secondary antibodies used were sheep anti-mouse HRP whole IgG (GE Healthcare life sciences, Pittsburgh, Pa., catalog no. RPN4201, and donkey anti-rabbit HRP whole IgG (GE Healthcare life sciences, Pittsburgh, Pa., catalog no. RPN4301).

5. Immunocytochemistry Staining 48 hours after HepG2 cells were grown on coverslips, they were transfected with pre-miR-185 and control miR. Cells were washed with PBS and fixed in 4% paraformaldehyde (Emsdiasum, Hatfield, Pa., catalog no. 15700) in PBS for 20 minutes at room temperature. Cells were then blocked at room temperature for 1 h in PBS containing 0.05% Triton X-100, 5% BSA. Rabbit anti-LDLR antibody was incubated with cells at room temperature for 2 hours. Following the addition of the primary antibody, Alexa Fluor 488-conjugated secondary antibody (Life Technology, Grand Island, N.Y. catalog no. A11008) was used. After antibody incubation, cells were washed with PBS and mounted with fluorescent mounting medium containing DAPI (Invitrogen, Life Technology, Grand Island, N.Y., catalog no. P36931) for counter staining. Fluorescent microscopy was performed using a 20× objective on a Leica DMI6000 confocal microscope, and images were processed using LAS AF software.

6. LDL Uptake Assay 24 hours after HepG2 cells were grown on coverslips they were transfected with pre-miR-185 and control miR. Cells were washed with PBS and incubated over night in sterol-deficient medium to induce the expression of LDLR. Uptake was initiated by incubating cells in serum-deficient medium containing 5 µg/ml BODIPY-LDL (Invitrogen, Life Technology Grand Island, N.Y., catalog number L3483). Uptake of BODIPY-LDL was measured after a 30 min incubation period at 37° C. Cells were washed with PBS containing 0.2% BSA and fixed in 4% paraformaldehyde (Emsdiasum) in PBS. Cells were then washed with PBS and mounted with fluorescent mounting medium containing DAPI (Invitrogen) for counter staining as described above. Intercellular BODIPY-LDL was visualized using fluorescent microscopy as described above.

7. HMGCR Activity Assay

HMGCR activity assay was performed as described previously (Favier et al., 1997; Shum, et al. 1998). 24 hours after HepG2 cells were transfected with pre-miR-185 or control pre-miR, cells were incubated with 5% LPDS over night to stimulate HMGCR activity. After lysing the cells, 100 µg of total protein was incubated at 37° C. for 30 min in reaction buffer (20 mM glucose-6-phophate, obtained from EMD, Millipore, Billerica, Mass., catalog no. 346764-1GM; 0.7 unit glucose-6-phosphate dehydrogenase, 3 mM NADPH and 5 mM DTT, obtained from Sigma, St. Louise Mo., catalog nos., G6378-100UN, N5755-100MG, and 43815-1G, respectively). The reaction was initiated by the addition of 30 µM $^{14}$C-HMG-CoA (American Radiolabeled Chemicals, St. Louis, Mo., catalog no. ARC1000-10 µCi). After a 2 hour incubation at 37° C., the reaction was stopped by the addition of 5N HCl (EMD, Millipore, Billerica, Mass. catalog no. GC0076) and 3 µmol of [$^3$H] mevalonolactone (21.8 mCi/mol) American Radiolabeled Chemicals, St. Louis, Mo., catalog no. ART0315-250 µCi) C-mevalonolactone was separated from unreacted $^{14}$C-HMG-CoA by column chromatography using AG1-X8 resion (200-400 mesh, Millipore). After the samples were added to the resin bed, seven 1 ml aliquots of water were used to elute $^{14}$C-mevalonolactone. The first 2 mL of aliquots were discarded, and the next 5 ml of elute were quantified using Liquid Scintillation Counter (Beckman Coulter). The HMGCR activity was determined by normalizing isolated [$^{14}$C]-mevalonolactone to the internal control, [$^3$H]-mevalonolactone.

8. Chromatin Immunoprecipitation

ChIP was performed using Imprint Chromatin Immunoprecipitation Kit (Sigma) following manufacturer's instructions. Immunoprecipitation was performed using anti-polyclonal rabbit SREBP-1c (Santa Cruz Biotechnology, Dallas, Tex., catalog no. sc-8924) antibody and rabbit IgG (Santa Cruz). PCR was performed for the promoter region of miR-185 using primers detecting the 50 bp-500 bp upstream from TSS:

```
F: ATCCCAGAGTAAAGGCAGATAAGG;      (SEQ ID NO: 6)
and

R: GCGGAGACATGTCATCTCC.           (SEQ ID NO: 7)
```

9. Electrophoretic Mobility Shift Assay (EMSA) and Gel Super-Shift

Nuclear extracts were prepared from HepG2 cells utilizing the Nuclear Extract Kit (Active Motif) (Carlsbad, Calif., catalog no. 40010) as described by the manufacturer. Wild-type (WT) and mutant probes were synthesized as single stranded oligonucleotides with Biotin 3'-end labeling (Integrated DNA technology) from the −100 to −139 and −225 to −261 region of the miR-185 putative promoter.

The sequences of the probes utilized were: Site 1 (putative SRE):

```
WT-F
                                            (SEQ ID NO: 8)
5'-CAGCAGCCTGGGTACTCACCTGAGGTTATTAGACAGCAGC -3'

WT-R
                                            (SEQ ID NO: 9)
5'-GCTGCTGTCTAATAACCTCAGGTGAGTACCCAGGCTGCTG -3'

M-F
                                            (SEQ ID NO: 10)
5'-CAGCAGCCTGGGTACCGGCAGGAGGTTATTAGACAGCAGC -3'

M-R
                                            (SEQ ID NO: 11)
5'-GCTGCTGTCTAATAACCTCCTGCCGGTACCCAGGCTGCTG -3'
```

Site 2 (putative SRE):

```
WT-F
                                            (SEQ ID NO: 12)
5'-GAGGCTGGAGCTCTCAGGCCACCTGCCCAGGGCGACTCCC -3'

WT-R
                                            (SEQ ID NO: 13)
5'-GGGAGTCGCCCTGGGCAGGTGGCCTGAGAGCTCCAGCCTC -3'

M-F
                                            (SEQ ID NO: 14)
5'-GAGGCTGGAGCTCCTCGCCTCGATGCCCAGGGCGACTCCC -3'

M-R
                                            (SEQ ID NO: 15)
5'-GGGAGTCGCCCTGGGCATCGAGGCGAGGAGCTCCAGCCTC -3'
(potential binding sites are underlined,
and mutated bases are bolded and underlined).
```

EMSA binding reactions were performed at room temperature for 20 min and consisted of the nuclear extract in 1× binding buffer (50% glycerol, 100 mM MgCl$_2$, 1 µg/µl Poly (dI-dC), 1% NP-40, 1 M KCl, 200 mM EDTA and 5 µM DNA probe). The mixture was run on 6% non-denaturing polyacrylamide gels in 0.5× Tris Borate-EDTA buffer. Protein-DNA complexes were then transferred to Hybond-N+ nylon membrane using the Trans-Blot semi-dry method (Bio-Rad, CA), and cross-linked using the Spectrolinker XL-1000 UV cross-linker (Spectronics Corporation, NY). Detection of biotin-labeled DNA was performed using the LightShift chemiluminsecent EMSA kit (Thermo Scientific, 20148) and visualized by exposure to a charge couple device camera (GE ImageQuant LAS 4000).

For comparison EMSA studies, 20-fold molar excess of the cold, WT non-biotin labeled site 1 forward and reverse oligonucleotides were added to the EMSA reaction mix. For the gel-Supershift assay, following the incubation of the nuclear extracts with site 2 WT miR-185 promoter probes, 4 µg of SREBP-1c mouse antibody (Santa Cruz Biotechnology, Dallas, Tex., catalog no. sc-8924) or 4 µg of GAPDH mouse control antibody (GeneTex Inc., Irvine, Calif.; catalog no. GT239) were added to the reaction mix and incubated at room temperature for 30 min. The mix was fractionated on a 5% non-denaturing polyacrylamide gel. Transfer and detection was performed as described above.

10. Mouse Studies

Wild type male C57BL/6J (B6) mice were purchased from Jackson Laboratory (Bar harbor, ME) and housed at Temple University, Philadelphia, Pa. Temple University Institutional Animal Care and Use Committee (IACUC) approved all experimental procedures. 6-8 weeks old male B6 mice were fed either a normal diet (7% fat) or a high fat diet (21% fat) for 16 weeks. Fasted blood samples were taken every four weeks. Blood serum was obtained and used to measure total cholesterol using the Total Cholesterol Kit (Stanbio, Borerne, Tex., catalog no. 0595-003) following manufacturer's protocol. Mice from each group were also sacrificed at weeks 4, 8, 12 and 16, and liver tissue was collected for protein and microRNA analysis.

11. Human Serum Study

Human normal serum samples (n=46) and hypercholesterolemic serum samples (n=40) were collected from Bioreclamation. All serum samples were from patients >50 years old. Mixed sex and race samples were used. Total RNA was extracted with TRIzol reagent (Invitrogen, Life Technology, Grand Island, catalog no. 1559618). cDNA was synthesized from total RNA using RT Easy First Strand Kit (Qiagen, Philadelphia, Pa., catalog no. 330421). qRT-PCR was carried out using a Stratagene MX3005P (Stratagene, Santa Clara, Calif.). mRNA levels were normalized to the level of GAPDH. In addition, small RNA was converted to complimentary DNA from 100 ng (human serum) or 500 ng (cell lines and mouse livers) of total RNA using the miScript II RT kit (Qiagen, Philadelphia, Pa., catalog no. 218160). The miR-185 level was determined by qRT-PCR using miScript SYBR Green PCR Kit (Qiagen, Philadelphia, Pa., catalog no. 218073) and miR specific (miR-185) primers (Qiagen, Philadelphia, Pa., catalog no. MS00001736) and normalizing to RNU6-2 (Qiagen, Philadelphia, Pa., catalog no. MS00033740) snRNA level as a control. For miR-185 levels in mouse liver, miR-185 expression was normalized to SNORD66 level. Data is shown as the ration of miR-185 expression as compared to either RNU-6 or SNORD66 (Qiagen, Philadelphia, Pa., catalog no. 331001).

12. Statistical Analyses

The presented experiments were from three independent repeats. The data present the means±s.e.m. Statistical analysis was performed using student's t-test.

All publications and patents cited in this specification are herein incorporated by reference in their entirety. Various modifications and variations of the described composition, method, and systems of the invention will be apparent to those skilled in the art without departing from the scope and spirit of the invention. Although the invention has been described in connection with specific preferred embodiments and certain working examples, it should be understood that the invention as claimed should not be unduly limited to such specific embodiments.

What is claimed is:

1. A method for reducing the expression level of SREBP-2 in a cell comprising the steps of:
   a) providing a cell in need of reducing the expression level of SREBP-2; and
   b) transfecting in said cell with a composition comprising a miR-185 precursor, said miR-185 precursor consisting of a nucleotide sequence set forth in SEQ ID NO: 1, wherein said transfecting step of said miR-185 precursor causes the inhibition of SREBP-2 in said cell.

2. The method of claim 1, wherein said SREBP-2 is a mRNA or a protein.

3. The method of claim 1, wherein said SREBP-2 is a mRNA.

* * * * *